United States Patent
Mehta et al.

(10) Patent No.: US 6,200,597 B1
(45) Date of Patent: *Mar. 13, 2001

(54) FORMULATION AND USE OF CAROTENOIDS IN TREATMENT OF CANCER

(75) Inventors: Kapil Mehta; Roman Perez-Soler; Gabriel Lopez-Berestein, all of Houston; Robert Lenk, Willis; Alan C. Hayman, deceased, late of The Woodlands, all of TX (US), by Katherine J. Hayman, legal representative

(73) Assignees: Board of Regents, The University of Texas System; Aronex Pharmaceuticals, Inc., both of Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/095,672

(22) Filed: Jun. 10, 1998

Related U.S. Application Data

(63) Continuation of application No. 08/735,310, filed on Oct. 22, 1996, now Pat. No. 5,811,119, which is a continuation of application No. 08/286,928, filed on Aug. 8, 1994, now abandoned, which is a continuation-in-part of application No. 08/213,249, filed on Mar. 14, 1994, now abandoned, which is a continuation of application No. 07/822,055, filed on Jan. 16, 1992, now abandoned, which is a continuation-in-part of application No. 07/588,143, filed on Sep. 25, 1990, now abandoned, which is a division of application No. 07/152,183, filed on Feb. 4, 1988, now abandoned, and a continuation-in-part of application No. 07/051,890, filed on May 19, 1987, now Pat. No. 4,863,739.

(51) Int. Cl.[7] .................................................. A61K 9/127
(52) U.S. Cl. ........................................... 424/450; 514/725
(58) Field of Search .................... 424/480, 489, 424/1.21, 9.321, 9.51, 417; 514/725

(56) References Cited

U.S. PATENT DOCUMENTS

| | | | |
|---|---|---|---|
| 3,993,754 | * | 11/1976 | Rahman ............................... 424/177 |
| 4,186,183 | * | 1/1980 | Steck et al. ............................ 424/38 |
| 4,235,871 | * | 11/1980 | Papahadjopoulos ................... 424/19 |
| 4,241,046 | * | 12/1980 | Papahadjopoulos ................... 424/19 |
| 4,311,712 | * | 1/1982 | Evans et al. .......................... 424/365 |
| 4,330,534 | * | 5/1982 | Sakurai et al. ....................... 424/182 |
| 4,370,349 | * | 1/1983 | Evans et al. ......................... 424/365 |
| 4,515,736 | * | 5/1985 | Deamer ................................ 264/4.3 |
| 4,522,803 | * | 6/1985 | Lenk et al. ............................ 424/1.1 |

(List continued on next page.)

FOREIGN PATENT DOCUMENTS

| | | | |
|---|---|---|---|
| 0170642 | * | 2/1986 | (EP) . |
| 0190926 | * | 8/1986 | (EP) . |

(List continued on next page.)

OTHER PUBLICATIONS

PCT/US93/00233 International Search Report, Jan. 13, 1993.*

PCT/US89/00435 International Search Report, Feb. 3, 1989.*

(List continued on next page.)

Primary Examiner—Gollamudi S. Kishore
(74) Attorney, Agent, or Firm—Fulbright & Jaworski L.L.P.

(57) ABSTRACT

A reduced-toxicity formulation of carotenoids is disclosed which is stable in an aqueous environment. The formulation includes a carotenoid, lipid arrier particles (such as liposomes), and an intercalation promoter agent (such as a triglyceride), which causes the carotenoid to be substantially uniformly distributed with the lipid in the lipid carrier particles. The molar ratio of carotenoid to lipid is greater than about 1:10. Also disclosed is a method of inhibiting the growth of cancer cells, which comprises administering to a living subject a therapeutically effective amount of a composition as described above.

6 Claims, 9 Drawing Sheets

U.S. PATENT DOCUMENTS

| | | | | |
|---|---|---|---|---|
| 4,610,868 | * | 9/1986 | Fountain et al. | 424/1.1 |
| 4,618,685 | * | 10/1986 | McCully | 549/63 |
| 4,663,167 | * | 5/1987 | Lopez-Berestein | 514/37 |
| 4,812,312 | * | 3/1989 | Lopez-Berestein | 424/417 |
| 4,818,537 | * | 4/1989 | Guo | 424/427 |
| 4,855,090 | * | 8/1989 | Wallach | 264/4.1 |
| 4,863,739 | * | 9/1989 | Perez-Soler et al. | 424/450 |
| 4,911,928 | * | 3/1990 | Wallach | 424/450 |
| 5,034,228 | * | 7/1991 | Meybeck et al. | 424/401 |
| 5,811,119 | * | 9/1998 | Mehta | 424/450 |

FOREIGN PATENT DOCUMENTS

| | | | | |
|---|---|---|---|---|
| 0198765 | * | 10/1986 | (EP) | |
| 0219922 | * | 4/1987 | (EP) | |
| 0229561 | * | 7/1987 | (EP) | |
| 0274174 | * | 7/1988 | (EP) | |
| 0287198 | * | 10/1988 | (EP) | |
| 2112426 | * | 6/1972 | (FR) | |
| 2455458 | * | 11/1980 | (FR) | |
| 2593394 | * | 7/1987 | (FR) | |
| 1575343 | * | 9/1980 | (GB) | |
| 2050287 | * | 1/1981 | (GB) | |
| WO87/01933 | * | 4/1987 | (WO) | |
| WO89/06977 | * | 8/1989 | (WO) | |
| WO89/11850 | * | 12/1989 | (WO) | |
| WO91/12794 | * | 9/1991 | (WO) | |
| WO93/13751 | * | 7/1993 | (WO) | A61K/9/127 |

OTHER PUBLICATIONS

PCT/US88/03831 International Search Report, Oct. 27, 1988.*

Davies, "Retinoic Acid–induced Expression of Tissue Transglutaminase in Human Promyelocytic Leukemia (HL–60) Cells," Journal of Biological Chemistry, 260(8):5166–5174 (Apr. 25, 1985).*

Roberts, "Cellular Biology and Biochemistry of the Retinoids," The Retinoids, 2:210–286 (1984).*

Dennert, "Retinoids and the Immune System: Immunostimulation by Vitamin A," The Retinoids, 2:373–390 (1984).*

Oppenheimer, "Cancer: A Biological and Clinical Introduction," Calif. St. University, Northridge, Second Edition, pp. 203–204 (1985).*

Jones, "Liposome Research: New Paths for Drug Delivery," Chemical Week, pp. 26–28 (Jul. 30, 1986).*

Mehta et al, "Amphotericin B Inhibits the Serum–Induced Expression of Tissue Transglutaminase in Murine Peritoneal Macrophages," J. Immunol., 136(11):4206–4212 (Jun. 1, 1986).*

Mehta et al, "Induction of Tissue Transglutaminase in Human Peripheral Blood Monocytes by Intracellular Delivery of Retinoids," J. of Leukocyte Biology, 41:341–348 (1987).*

Mehta et al, "Suppression of Macrophage Cytostatic Activation by Serum Retinoids: A Possible Role for Transglutaminase," J. Immunology, 138(11):3902–3906 (Jun. 1, 1987).*

Stillwell et al, "Effect of Retinol and Retinoic Acid on Permeability, Electrical Resistance and Phase Transition of Lipid Bilayers," Biochimica et Biophysica Acta, 688:653–659 (1982).*

Gurrieri et al, "Thermotropic Behavior of Dipalmitoylphosphatidylcholine Liposomes Containing Retinoids," Thermochimica Acta, 122:117–122 (1987).*

Fex et al, "Retinol Transfer Across and Between Phospholipid Bilayer Membranes," Biochem. et Biophysica Acta, 944:249–255 (1988).*

Szoka et al, "Comparative Properties and Methods of Preparation of Lipid Vesicles (Liposomes)," Ann. Rev. Biophys. Bioeng., 9:467–508 (1980).*

Cuatrecasas, "Hormone Receptor, Membrane Phospholipids, and Protein Kinases," The Harvey Lectures, Series 80, pp. 89–129 (1986).*

Ferrero et al, "Induction of Differentiation of Human Myeloid Leukemias: Surface Changes Probed With Monoclonal Antibodies," Blood, 61(1):171–179 (Jan. 1983).*

Ganguly et al, "Systemic Mode of Action of Vitamin A," Vitamins and Hormones, vol. 38:1–54 (1980).*

Heller et al, "Conformational Changes Following Interaction Between Retinol Isomers and Human Retinol–binding Protein and Between the Retinol–binding Protein and Prealbumin," J. of Biological Chem., 248(18): 6308–6316 (Sep. 25, 1973).*

Leu et al, "Enhanced Transglutaminase Activity Associated with Macrophage Activation," Experimental Cell Research, 141:191–199 (1982).*

Leibovich et al, "The Role of the Macrophage in Wound Repair," Amer. J. of Pathology, 78(1):71–98 (Jan. 1975).*

Lopez–Berestein et al, "Comparative Functional Analysis of Lymphoctyes and Monocytes from Plateletapheresis," Transfusion, 23:201–206 (1983).*

Lorand et al, "Amine Specificity in Transpeptidation. Inhibition of Fibrin Cross–Linking," Biochemistry, 7(3):1214–1223 (Mar. 1968).*

Lowry et al, "Protein Measurement with the Folin Phenol Reagent," Dept. of Pharmacology, Washington Univ. School of Med., pp. 265–275 (May 25, 1951).*

Mehta et al, "Stimulation of Macrophase Protease Secretion Via Liposomal Delivery of Muramyl Dipeptide Derivatives to Intracellular Sites," Immunology, 51:517–527 (1984).*

Mehta et al, "Expression of Tissue Transglutaminase in Cultured Monocytic Leukemia (THP–1) Cells During Differentiation," Cancer Research, 46:1388–1394 (Mar. 1986).*

Mehta et al, "Uptake of Liposomes and Liopsome–Encapsulated Muramyl Dipeptide by Human Peripheral Blood Monocytes," J. of the Retinculoendothelial Society, 32:155–164 (1982).*

Mehta et al, "Interferon–γ Requires Serum Retinoids to Promote the Expression of Tissue Transglutaminase in Cultured Human Blood Monocytes," J. of Immunology, 134(4):2053–2056 (Apr. 1985).*

Mehta et al, "Phagocytosis Inhibits the Expression of Tissue Transglutaminase in Mouse Peritoneal Macrophages," J. Immunology, 132(5):2552–2558 (May 1984).*

Moore et al, "Retinoic Acid–induced Expression of Tissue Transglutaminase in Mouse Peritoneal Macrophages," J. of Biological Chemistry, 259(20): 12794–12802 (Oct. 25, 1984).*

Murtaugh et al, "Induction of Tissue Transglutaminase in Human Peripheral Blood Monocytes," J. Exp. Med., 159:114–125, (Jan. 1984).*

Murtaugh et al "Retinoic Acid–Induced Gene Expression in Normal and Leukemic Myeloid Cells," J. Exp. Med., 163:1325–1330 (May 1986).*

Murtaugh et al, "Induction of Tissue Transglutaminase in Mouse Peritoneal Macrophages," J. of Biological Chemistry, 258(18):11074–11081 (Sep. 25, 1983).*

D.S. Nelson, "Macrophages as Effectors of Cell–Mediated Immunity," CRC Critical Reviews in Microbiology, pp. 353–384 (Feb. 1972).*

Normann et al, "Cytotoxicity of Human Peripheral Blood Monocytes," Cellular Immunology, 81:413–425 (1983).*

Norris et al, "Isolation of Functional Subsets of Human Peripheral Blood Monocytes," J. Immunology, 123(1):166–172 (Jul. 1979).*

Olsson et al, "Induction of Differentiation of the Human Histiocytic Lymphoma Cell Line U–937 by Retinoic Acid and Cyclic Adenosine 3':5'–Mono–phosphate–inducing Agents," Cancer Research, 42:3924–3927 (Oct. 1982).*

Peterson, "Characteristics of a Vitamin A–transporting Protein Complex Occurring in Human Serum," J. of Biological Chem., 246(1):34–43 (Jan. 10, 1971).*

Picker et al, "Metabolic Heterogeneity Among Human Monocytes and its Modulation by PGE," J. Immunology, 124(6):2557–2562 (Jun. 1980).*

Rask et al, "In Vitro Uptake of Vitamin A From the Retinol–binding Plasma Protein to Mucosal Epithelial Cells from the Monkey's Small Intestine," J. of Biological Chem., 251(20):6360–6366 (Oct. 25, 1976).*

Rothblat et al, "Preparation of Delipidized Serum Protein for Use in Cell Culture Systems," In Vitro, 12(8):554–556 (1976).*

Schroff et al, "Transglutaminase as a Marker for Subsets of Murine Macrophages," Eur. J. Immunol., 11:637–642 (1981).*

Scott et al, "Retinoids Increase Transglutaminase Activity and Inhibit Ornithine Decarboxylase Activity in Chinese Hamster Ovary Cells and in Melanoma Cells Stimulated to Differentiate," Proc. Natl. Acad. Sci. USA, 79:4093–4097 (Jul. 1982).*

Turpin et al, "Charcterization of Small and Large Human Peripheral Blood Monocytes: Effects of In Vitro Maturation on Hydrogen Peroxide Release and on the Response to Macrophage Activators," J. Immunology, 136(11): 4194–4198 (Jun. 1, 1986).*

Yuspa et al, "Regulation of Epidermal Transglutaminase Activity and Terminal Differentiation by Retinoids and Phorbol Esters," Cancer Research, 43:5707–5712 (Dec. 1983).*

Yuspa et al, "Retinoic Acid Induces Transglutaminase Activity but Inhibits Cornification of Cultured Epidermal Cells," J. of Biological Chem., 257(17):9906–9908 (Sep. 10, 1982).*

Mehta et al, "Liposome–encapsulated all–trans retinoic acid circumvents retinoid 'resistance' in rats", Proceedings of the American Association for Cancer Research, 34:26/150 (Mar. 1993).*

Lee et al, "Phase I Evaluation of All–Trans–Retinoic Acid in Adults with Solid Tumors", J. of Clinical Oncology, 11(5):959–966 (May 1993).*

Muindi et al, "Continuous Treatment with All–Trans Retinoic Acid Causes a Progressive Reduction in Plasma Drug Concentrations: Implications for Relapse and Retinoid 'Resistance' in Patients with Acute Promyelocytic Leukemia", Blood, 79(2):299–303 (Jan. 15, 1992).*

Lautersztain et al, "Cellular Pharmacology of Liposomal cis–Bis–neodeca–noato–trans–R,R–1,2–diaminocyclohexaneplatinum (II) in Mouse Resident Peritoneal Macrophages, Kupffer Cells, and Hepatocytes", Cancer Research, 48:1300–1306 (1988).*

Perez–Soler et al, "Toxicity and Antitumor Activity of cis–Bis–cyclopen–tenecarboxylato–1,2–diaminocyclohexane Platinum (II) Encapsulated in Multilamellar Vesicles", Cancer Research, 46:6269–6273 (Dec. 1986).*

Kamm et al, "Preclinical and Clinical Toxicology of Selected Retinoids", The Retinoids, 2:287–326 (1984).*

Reuben Lotan, "Effects of Vitamin A and its Analogs (Retinoids) on Normal and Neoplastic Cells", Biochimica et Biophysica Acta, 605:33–91 (1980).*

Breitman et al, "Induction of differentiation of the human promyelocytic leukemia cell line (HL–60) by retinoic acid", Proceedings of the National Academy of Sciences, 77(5):2355–3072 (May 1980).*

Hayes et al, "Toxicity of the Vitamins", Toxicants Occurring Naturally in Foods, 2d Ed. 235–253 (1973).*

Bertram et al, "Inhibition of In Vitro Neoplastic Transformation by Retinoids", Molecular Interrelations of Nutrition and Cancer, 315–335 (1982).*

Carmia Borek, "Vitamins and Micronutrients Modify Carcinogenesis and Tumor Promotion in Vitro", Molecular Interrelations of Nutrition and Cancer, 337–350 (1982).*

Sporn et al, "Retinoids and Chemoprevention of Cancer", Laboratory of Chemoprevention, National Cancer Institute, Bethesda, Maryland, 20205, 71–100.*

Strickland, "Mouse Teratocarcinoma Cells: Prospects for the Study of Embryogenesis and Neoplasia", Cell, 24:277–278 (May 1981).*

Lippman et al, "Retinoids as Preventive and Therapeutic Anticancer Agents (Part II)", Cancer Treatment Reports, 71(5):493–515 (May 1987).*

Sporn et al, "Prevention of chemical carcinogenesis by vitamin A and its synthetic analogs (retinoids)", Federation Proceedings, 35(6):1332–1338 (May 1, 1976).*

Sporn et al, "Chemoprevention of cancer with retinoids", Federation Proceedings, 38(11):2528–2534 (Oct. 1979).*

W. Bollag, "Retinoids and Cancer", Cancer Chemotherapy and Pharmacology, 3:207–215 (1979).*

Lotan et al, "Suppression of the Transformed Cell Phenotype Expression by Retinoids", Modulation and Mediation of Cancer by Vitamins, 211–222 (1983).*

Juliano et al, "Liposomes as a drug delivery system", Drug Delivery Systems: Characteristics and Biomedical Applications, 189–237 (1980).*

Juliano, "Pharmacokinetics of liposome–encapsulated drugs", Liposomes: From Physical Structure to Therapeutic Applications, 391–407 (1981).*

Wolbach et al, "Tissue Changes Following Deprivation of Fat–Soluble A Vitamin", The Journal of Experimental Medicine, 42:753–777 (Sep. 4, 1925).*

Saffiotti et al, "Experimental Cancer of the Lung: Inhibition by Vitamin A of the Induction of Tracheobronchial Squamous Metaplasia and Squamous Cell Tumors", Cancer:Jour. of Amer. Cancer Society, 20:857–864 (1967).*

Breitman et al, "Terminal Differentiation of Human Promyelocytic Leukemic Cells in Primary Culture in Response to Retinoic Acid", Blood 57(6): 1000–1004 (Jun. 1981).*

Mehta et al, "Expression of Tissue Transglutaminase in Cultured Monocytic Leukemia (THP–1) Cells During Differentiation", Cancer Research, 46:1388–1394 (Mar. 1986).*

Mayer et al, "Retinoids, a new class of compounds with prophylactic and therapeutic activities in oncology and dermatology", Experientia, 34(9):1105–1119 (Sep. 1978).*

* cited by examiner

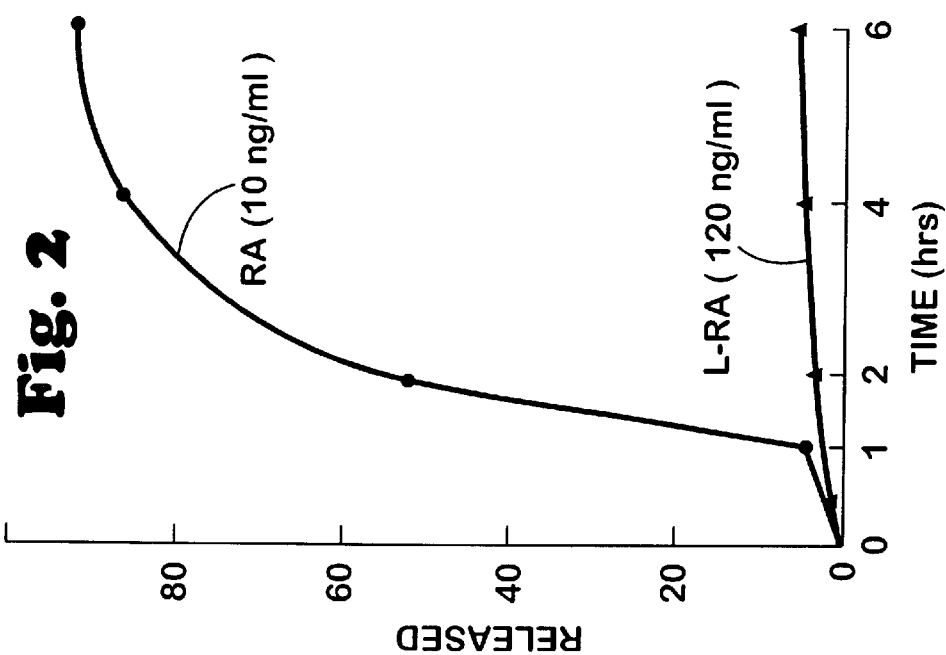
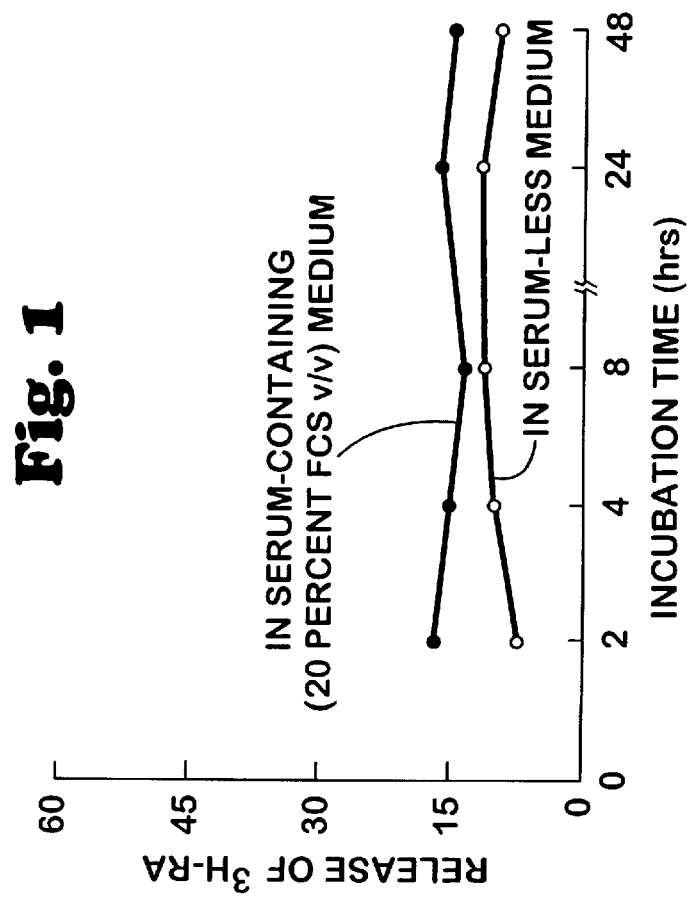

1 2 3 4 5

1 2 3 4

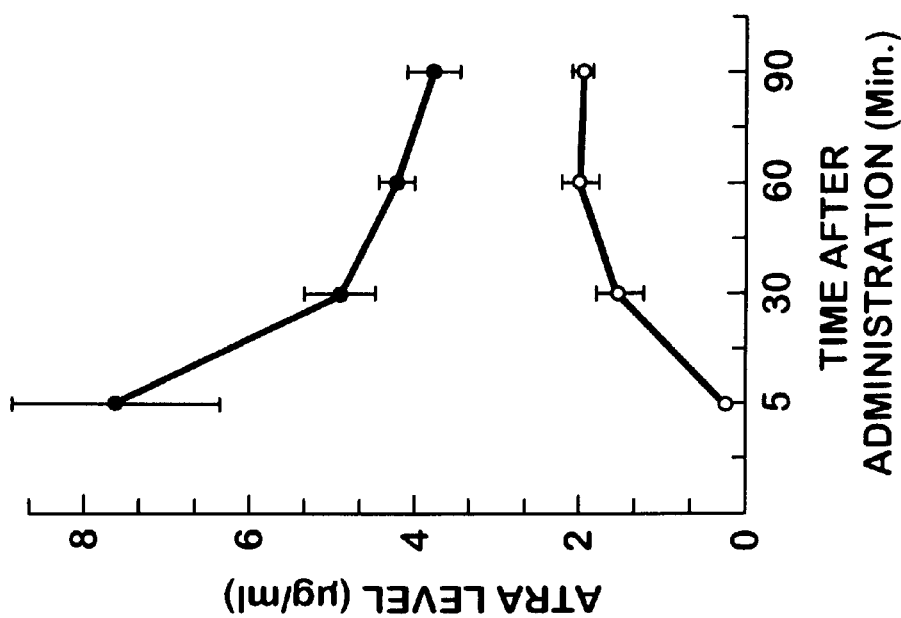
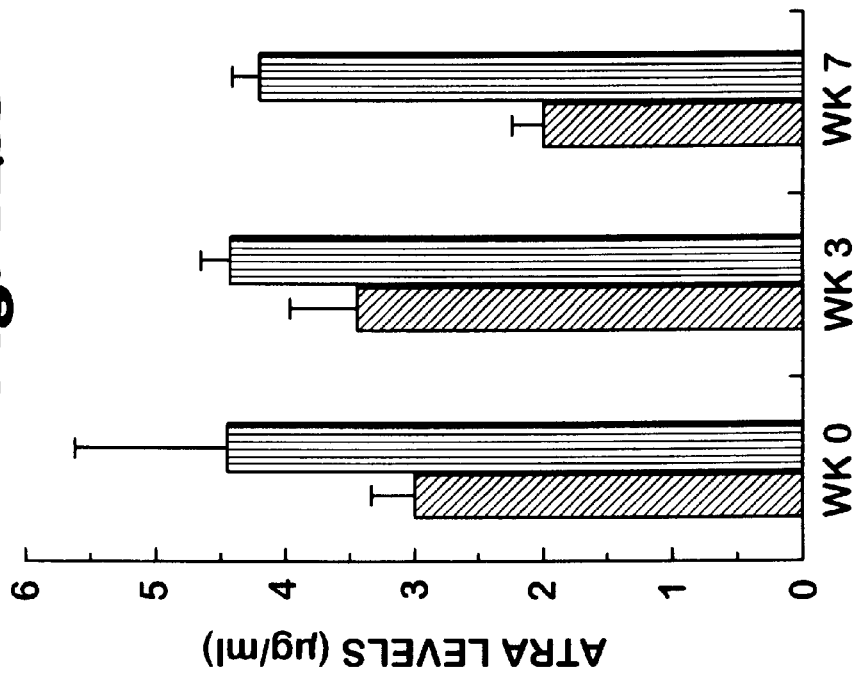

FORMULATION AND USE OF CAROTENOIDS IN TREATMENT OF CANCER

CROSS-REFERENCE TO RELATED APPLICATIONS

This application is a continuation of U.S. Ser. No. 08/735,310, filed on Oct. 22, 1996, issued as U.S. Pat. No. 5,811,119, Sep. 22, 1998 which is a continuation of U.S. Ser. No. 08/286,928, filed on Aug. 8, 1994, now abandoned, a continuation-in-part of U.S. Ser. No. 08/213,249, filed on Mar. 14, 1994, now abandoned which is a continuation of U.S. Ser. No. 07/822,055, filed on Jan. 16, 1992, now abandoned, which is a continuation-in-part of U.S. Ser. No. 07/588,143, filed on Sep. 25, 1990, now abandoned, which is a divisional of U.S. Ser. No. 07/152,183, filed on Feb. 4, 1988, now abandoned. The application Ser. No. 07/152,183 is also a continuation in part of U.S. Ser. No. 07/051,890, filed on May 19, 1987, issued as U.S. Pat. No. 4,863,739, Sep. 5, 1989. The above-identified applications are incorporated here by reference.

BACKGROUND OF THE INVENTION

The present invention relates to therapeutic compositions of carotenoids encapsulated in liposomes or other lipid carrier particles.

It has been known for more than 50 years that retinoids, the family of molecules comprising both the natural and synthetic analogues of retinol (vitamin A), are potent agents for control of both cellular differentiation and cellular proliferation (Wolbach et al., J. Exp. Med., 42:753–777, 1925). Several studies have shown that retinoids can suppress the process of carcinogenesis in vivo in experimental animals (for reviews, see e.g., Bollag, Cancer Chemother. Pharmacol., 3:207–215, 1979, and Sporn et al., In Zedeck et al. (eds.), Inhibition of Tumor induction and development, pp. 71–100. New York: Plenum Publishing Corp., 1981). These results are now the basis of current attempts to use retinoids for cancer prevention in humans. Furthermore, there is extensive evidence which suggests that retinoids can suppress the development of malignant phenotype in vitro (for review, see e.g., Bertram et al., In: M. S. Arnott et al., (eds.), Molecular interactions of nutrition and cancer, pp 315–335. New York, Raven Press, 1982; Lotan et al., The modulation and mediation of cancer by vitamins, pp 211–223. Basel: S. Karger AG, 1983) thus suggesting a potential use of retinoids in cancer prevention. Also, recently it has been shown that retinoids can exert effects on certain fully transformed, invasive, neoplastic cells leading in certain instances to a suppression of proliferation (Lotan, Biochim. Biophys. Acta, 605:33–91, 1980) and in other instances to terminal differentiation of these cells, resulting in a more benign, non-neoplastic phenotype (see e.g., Brietman et al., Proc. Natl. Acad. Sci. U.S.A., 77:2936–2940, 1980).

Retinoids have also been shown to be effective in the treatment of cystic acne (see e.g., Peck, et al., New Engl. J. Med., 300:329–333, 1979). In addition to cystic acne, retinoid therapy has been shown to be effective in gram-negative folliculitis, acne fulminans, acne conglobata, hidradenitis suppurativa, dissecting cellulitis of the scalp, and acne rosacea (see e.g., Plewig et al., J. Am. Acad. Dermatol., 6:766–785, 1982).

However, due to highly toxic side effects of naturally occurring forms of vitamin A (hypervitaminosis A) at therapeutic dose level, clinical use of retinoids has been limited (Kamm et al., In: The Retinoids. Sporn et al., (eds.), Academic Press, New York, pp 228–326, 1984; Lippman et al., Cancer Treatment Reports, 71:493–515, 1987). In free form, the retinoids may have access to the surrounding normal tissues which might be the basis of their profound toxicity to liver, central nervous system, and skeletal tissue.

Therefore, one potential method to reduce the toxicity associated with retinoid administration would be the use of a drug delivery system. The liposomal format is a useful one for controlling the topography of drug distribution in vivo. This, in essence, involves attaining a high concentration and/or long duration of drug action at a target (e.g. a tumor) site where beneficial effects may occur, while maintaining a low concentration and/or reduced duration at other sites where adverse side effects may occur (Juliano, et al., In: Drug Delivery Systems, Juliano ed., Oxford Press, New York, pp 189–230, 1980). Liposome-encapsulation of drug may be expected to impact upon all the problems of controlled drug delivery since encapsulation radically alters the pharmacokinetics, distribution and metabolism of drugs.

There are additional difficulties in using a liposomal formulation of a retinoid for therapeutic purposes. For example, it is often desirable to store the composition in the form of a preliposomal powder, but many prior formulations are not satisfactory for such use, because they either contain an inadequate amount of retinoid, or they generate undesirable liposomes when they are reconstituted in aqueous solution.

For compositions that are to be administered intravenously, typically the composition must provide at least about 100 mg of the active ingredient in a single container; if it contains a lesser amount of the active ingredient, an impractically large number of vials will be needed for dosing a single patient.

Typically a vial having a volume of 120 cc is the largest that can be accommodated in a commercial freeze drier, and 50 cc is the maximum volume of liquid that can be filled in such a vial. If more than 1 g of lipids are included in 50 cc of liquid volume, the resulting liposomes after reconstitution have a size distribution which is not acceptable for parenteral administration. This is because the packing of the lipids during lyophilization is affected by the concentration of the lipids in the solution. Thus, the concentration of lipids in the solution must be limited. However, when this is done in previously-known liposomal retinoid formulations, the retinoid tends to crystallize, and separate from the liposomes shortly after reconstitution.

In order to both limit the concentration of lipids and supply a sufficient amount of retinoid, it is necessary to provide a molar ratio of retinoid to lipid greater than about 1 to 10. Previously known formulations have not had, and are believed not to be capable of having such a high packing of retinoid in the liposomes. Therefore, a need exists for improved compositions and methods which will minimize or eliminate the problems of the prior art.

SUMMARY OF THE INVENTION

The present invention relates to therapeutically useful, reduced toxicity compositions of carotenoids. The compositions comprise a carotenoid, lipid carrier particles, and an intercalation promoter agent. "Carotenoid" is used here to include retinoids, pro-retinoids, carotenes, xanthophylls, and analogs thereof. A preferred example is all-trans retinoic acid. The carotenoid is substantially uniformly distributed with the lipid in the lipid carrier particles. More particularly, the carotenoid is substantially uniformly distributed in an intercalated position throughout a hydrophobic portion of the lipid carrier particles, as opposed to the aqueous phase. "Substantially uniformly distributed" means that at least 50% of the lipid carrier particles will contain carotenoid in a molar ratio between about 5:85 carotenoid:lipid and about 15:70. Preferably at least 75% of all lipid carrier particles will contain such a ratio of the active ingredient.

The composition is stable in an aqueous environment. In this context, "stable in an aqueous environment" means that the composition (1) will not exhibit any therapeutically significant degradation over a period of at least 24 hours, (2) will not exhibit a substantial degree of fusions of liposomes over that same period, and (3) will not exhibit substantial redistribution of the carotenoid over that same period, including no substantial movement of the drug into the aqueous phase of a liposome, and no substantial state change into a crystalline form.

The molar ratio of carotenoid to lipid in the lipid carrier particles is greater than about 1:10, and is most preferably at least about 15:85. The intercalation promoter agent preferably comprises at least about 15% by weight of the composition, and can suitably be, for example, a triglyceride.

"Lipid carrier particles" is used here to include liposomes, having a bilayer structure formed of one or more lipids having polar heads and nonpolar tails, as well as micelles, amorphous particulates of lipid, and other lipid emulsion state entities. When the particles are liposomes, suitable forms include multilamellar liposomes.

The present invention also relates to a pharmaceutical unit dosage formulation of a carotenoid, which comprises a carotenoid, lipid carrier particles, an intercalation promoter agent, and a pharmaceutically acceptable carrier. As stated above, the carotenoid is substantially uniformly distributed with the lipid in the lipid carrier particles, and the composition is stable in an aqueous environment.

In another aspect, the invention relates to a method of inhibiting the growth of cancer cells, in which a therapeutically effective amount of a carotenoid composition is administered to a living subject. The carotenoid composition can be as described above. The composition is preferably administered to the subject in a maintained molar ratio between about 5:85 carotenoid:lipid and about 15:70. "Maintained" in this context means that the stated ratio of drug to lipid lasts for at least 24 hours.

The present invention provides the therapeutic benefits of the carotenoid, while substantially reducing the undesirable toxicity of the composition, as compared to the free drug. For example, encapsulation of retinoic acid in liposomes results in a decrease of at least 15-fold in toxicity as compared to the free drug.

Further, the presence of the intercalation promoter agent permits the ratio of active ingredient to lipid to be increased above what has been previously known, and thus makes such formulations useful in a practical sense for lyophilization into a powder, and subsequent reconstitution into solution which can be administered parenterally to a patient. Without wishing to be bound by any particular theory, it is believed that the intercalation promoter agent overcomes steric hindrance that otherwise limits the amount of carotenoid that be incorporated in, for example, a liposome.

The encapsulation of carotenoids within, e.g., liposomes, permits their direct delivery to intracellular sites and thus circumvents the requirement for cell surface receptors. This may be of particular significance, for example, in therapy of tumors which lack the cell surface receptors for serum retinol binding protein but possess intracellular receptors for retinoic acid.

Compositions of the present invention are also substantially improved over prior liposomal retinoid formulations in terms of uniformity of drug distribution. Prior compositions often had substantial percentages of liposomes which contained essentially no drug. In the present invention, at least 50% and preferably at least 75% of all liposomes in the composition contain drug with the range specified above.

While not being bound by any particular theory of action, it has been found that, surprisingly, liposome encapsulation of carotenoids and particularly all-trans retinoic acid, circumvents the usual hepatic clearance mechanisms. This has resulted in a substantial extension of the efficacy of liposomal carotenoid over free carotenoid or retinoid. It is believed that liposomal all-trans retinoic acid avoids the problems of resistance to non-liposomal all-trans retinoic acid. This resistance is displayed by such parameters as reduced serum concentration upon prolonged treatment typically observed in treatments as extended over 2, 5 or 7 weeks or longer. Here, substantially longer periods of drug administration were unaccompanied by reduced circulating drug levels. Therapeutic i.v. dosages of 15 mg/m$^2$, 30 mg/m$^2$, 60 mg/m$^2$, 75 mg/m$^2$, and 90 mg/m$^2$, and further including 150 mg/m$^2$, 300 mg/m$^2$ and higher are noted. Regimens of therapy extending in excess of 7 weeks, and further in excess of 14 weeks, and further exhibiting non-declining drug levels are particularly noted. Regimens of administration of all-trans retinoic acid that avoid retinoid resistance are particularly noted herein, which includes administration of liposomal all-trans retinoic acid, and in one embodiment includes the retinoid being intercalated in the liposomal bilayer in substantially uncrystallized form.

In vivo administration of liposomal all-trans retinoic acid over a prolonged period did not exhibit declining blood levels. In vitro studies of isolated liver microsomes revealed unchanged catabolism upon repeated exposure to liposomal all-trans retinoic acid. In contrast, microsomes isolated from subjects originally administered non-liposomal all-trans retinoic acid an equal number of times displayed increased metabolism of all-trans retinoic acid.

Test data has indicated that the instant liposomal carotenoid formulations avoid "retinoid" resistance upon chronic i.v. administration. The results suggest that chronic administration of liposomal carotenoid, and particularly all-trans retinoic acid, does not affect the levels of circulating drug in subjects. While phospholipids are preferred, the broad grouping of lipids are useful in forming particular liposomes. Liver microsomes from test animals did not show any significant change in their ability to metabolize all-trans retinoic acid. In contrast, long-term oral administration of non-liposomal all-trans retinoic acid caused a significant decrease in circulating drug levels after 7 weeks of treatment. Liver microsomes from these animals converted all-trans retinoic acid into polar products much more rapidly than microsomes obtained from liposomal all-trans retinoic acid-treated or untreated animals.

BRIEF DESCRIPTION OF THE DRAWINGS

FIG. 1 shows a time profile of liposomal retinoic acid (L-RA) stability in the presence (●) and absence (O) of serum.

FIG. 2 shows human red blood cell (RBC) lysis as a function of time with RA (●) and L-RA (▲).

FIG. 12(A) shows the levels of all-trans retinoic acid in the blood 60 min after oral administration of non-liposomal all-trans retinoic acid or i.v. administration of liposomal all-trans retinoic acid.

FIG. 12(B) shows blood clearance of all-trans retinoic acid following administration of the last dose of all-trans retinoic acid.

DETAILED DESCRIPTION OF SPECIFIC EMBODIMENTS

Figure 4:
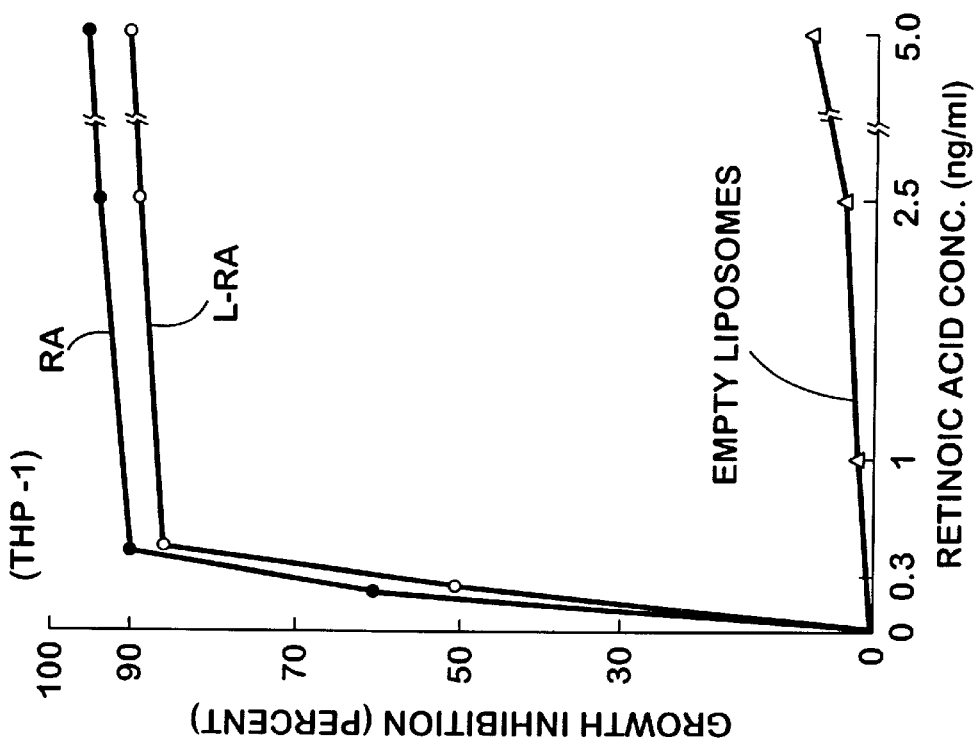
FIG. 4 shows the inhibition of THP-1 cell growth as a function of RA concentration (●), L-RA concentration (O) or empty liposome concentration (Δ).

Suitable therapeutic carotenoids for encapsulation in accordance with the present invention include various retinoids. Trans-retinoic acid and all-trans-retinol are preferred. Other retinoids that are believed suitable include: retinoic acid methyl ester, retinoic acid ethyl ester, phenyl analog of retinoic acid, etretinate, retinol, retinyl acetate, retinaldehyde, all-trans-retinoic acid, and 13-cis-retinoic acid.

Lipid carrier particles, such as liposomes, can be formed by methods that are well known in this field. Suitable phospholipid compounds include phosphatidyl choline, phosphatidic acid, phosphatidyl serine, sphingolipids, sphingomyelin, cardiolipin, glycolipids, gangliosides, cerebrosides, phosphatides, sterols, and the like. More particularly, the phospholipids which can be used include dimyristoyl phosphatidyl choline, egg phosphatidyl choline, dilauryloyl phosphatidyl choline, dipalmitoyl phosphatidyl choline, distearoyl phosphatidyl choline, 1-myristoyl-2-palmitoyl phosphatidyl choline, 1-palmitoyl-2-myristoyl phosphatidyl choline, 1-palmitoyl-2-stearoyl phosphatidyl choline, 1-stearoyl-2-palmitoyl phosphatidyl choline, dioleoyl phosphatidyl choline, dimyristoyl phosphatidic acid, dipalmitoyl phosphatidic acid, dimyristoyl phosphatidyl ethanolamine, dipalmitoyl phosphatidyl ethanolamine, dimyristoyl phosphatidyl serine, dipalmitoyl phosphatidyl serine, brain phosphatidyl serine, brain sphingomyelin, dipalmitoyl sphingomyelin, and distearoyl sphingomyelin.

Phosphatidyl glycerol, more particularly dimyristoyl phosphatidyl glycerol (DMPG), is not preferred for use in the present invention. In the carotenoid compositions of the present invention, the presence of DMPG correlates with the appearance of amorphous structures of anomalous size, which are believed to render the composition much less suitable for intravenous administration. When DMPG is omitted, the amorphous structures are not observed. The undesirable effects that are apparently caused by the presence of DMPG may result from the fact that DMPG has a negative charge, which may interact with the carboxylate of the carotenoid.

In addition, other lipids such as steroids and cholesterol may be intermixed with the phospholipid components to confer certain desired and known properties on the resultant liposomes. Further, synthetic phospholipids containing either altered aliphatic portions, such as hydroxyl groups, branched carbon chains, cyclo derivatives, aromatic derivatives, ethers, amides, polyunsaturated derivatives, halogenated derivatives, or altered hydrophilic portions containing carbohydrate, glycol, phosphate, phosphonate, quaternary amine, sulfate, sulfonate, carboxy, amine, sulfhydryl, imidazole groups and combinations of such groups, can be either substituted or intermixed with the phospholipids, and others known to those skilled in the art.

A suitable intercalation promoter agent will permit the high molar ratio of carotenoid to lipid that is desired for the present invention, without substantial crystallization from the liposomes after they are reconstituted in aqueous solution, as can be observed by microscopic analysis, separation techniques based on buoyant density, or other techniques well known to those skilled in the art. Triglycerides are preferred intercalation promoter agents, with soybean oil as one specific example. Other suitable agents include sterols, such as cholesterol, fatty alcohols, fatty acids, fatty acids esterified to a number of moieties, such as polysorbate, propylene glycol, mono- and diglycerides, and polymers such as polyvinyl alcohols.

Prior to lyophilization, the carotenoid, lipids, and intercalation promoter agent can be dissolved in an organic solvent, such as t-butanol. Lyophilization to form a preliposomal powder can be performed using commercial apparatus which is known to persons skilled in this field. After lyophilization, the powder can be reconstituted as, e.g., liposomes, by adding a pharmaceutically acceptable carrier, such as sterile water, saline solution, or dextrose solution, with agitation, and optionally with the application of heat.

A preferred formulation, which can be dissolved in 45 ml of t-butanol, is as follows:

| component | mg | millimoles | mole % | wt % |
|---|---|---|---|---|
| DMPC | 850 | 1.28 | 72 | 77 |
| soybean oil | 150 | 0.17 | 9 | 14 |
| tretinoin | 100 | 0.33 | 19 | 9 |

A composition of the present invention is preferably administered to a patient parenterally, for example by intravenous, intraarterial, intramuscular, intralymphatic, intraperitoneal, subcutaneous, intrapleural, or intrathecal injection. Administration could also be by topical application or oral dosage. Preferred dosages are between 40–200 mg/m$^2$. The dosage is preferably repeated on a timed schedule until tumor regression or disappearance has been achieved, and may be in conjunction with other forms of tumor therapy such as surgery, radiation, or chemotherapy with other agents.

The present invention is useful in the treatment of cancer, including the following specific examples: hematologic malignancies such as leukemia and lymphoma, carcinomas such as breast, lung, and colon, and sarcomas such as Kaposi's sarcoma.

EXAMPLE 1

Preparation of Liposomal-all Trans-retinoic Acid (L-RA)

Preparation of lyophilized powder containing all trans-retinoic acid and phospholipids was carried out as follows. A solution of retinoic acid in t-butanol (1–5 mg/ml) was added to a dry lipid film containing dimyristoyl phosphatidyl choline (DMPC) and dimyristoyl phosphatidyl glycerol (DMPG) at a 7:3 molar ratio. The phospholipids were solubilized in the t-butanol containing the all-trans retinoic acid and the solution was freeze-dried overnight. A powder containiny dimyristoyl phosphatidyl choline (DMPC), dimyristoyl phosphatidyl glycerol (DMPG), and all-trans retinoic acid was obtained. The lipid:drug ratio used was from 10:1 to 15:1.

Reconstitution of liposomal retinoic acid from the lyophilized powder was done as follows. The lyophilized powder was mixed with normal saline at room temperature to form multilamellar liposomes containing all trans-retinoic acid. This reconstitution method required mild hand-shaking for 1 min to obtain a preparation devoid of any aggregates or clumps. By light microscopy, the reconstituted preparation contained multilamellar liposomes of a close size range. No aggregates or drug clumps were identified in the liposomal preparation in three different experiments.

Encapsulation efficiency and size distribution of the liposomal all-trans retinoic acid preparation were determined as follows. The liposomal all-trans retinoic acid preparation was centrifuged at 30,000×g for 45 minutes. A yellowish pellet containing the retinoic acid and the lipids was obtained. By light microscopy, the pellet was composed of liposomes with no crystals or drug aggregates. The encapsulation efficiency was calculated to be greater than 90% by measuring the amount of free retinoic acid in the supernatant by UV spectrophotometry. Liposomes were sized in a Coulter-Counter and Channelizer. The size distribution was as follows: 27% of liposomes less than 2 micrometers ($\mu$m), 65% between 2 $\mu$m and 3 $\mu$m, 14% between 3 $\mu$m and 5 $\mu$m, 1% more than 5 $\mu$m. The method used for encapsulation of retinoids was simple, reproducible and could be used for large scale production, for example, for clinical trials.

Further experiments were performed by the same procedure but with different lipids, ratios of lipids and the use of $^3$H-all-trans retinoic acid. Additional lipids utilized were dipalmitoyl phosphatidyl choline (DPPC) stearylamine (SA) and cholesterol. After sedimentation of the liposomes, residual $^3$H was determined and encapsulation efficiency calculated. Table 1 shows encapsulation efficiencies determined by this method for various L-RA preparations.

TABLE 1

Encapsulation Efficiency of Retinoic Acid in Liposomes

| LIPOSOME COMPOSITION | ENCAPSULATION EFFICIENCY (%) |
|---|---|
| DMPC:cholesterol 9:1 | 69.3 |
| DMPC:cholesterol 9:3 | 64.5 |
| DPPC | 69.1 |
| DMPC:SA:cholesterol 8:1:1 | 56.7 |
| DMPC:DMPG 7:3 | 90 |
| DMPC:DMPG 9:1 | 90.7 |

Of the lipid compositions studied, DMPC:DMPG at ratios between 7:3 and 9:1 gave superior encapsulation efficiencies. Liposomal all-trans retinol (L-ROH) was prepared by the methods described above for L-RA with DMPC:DMPG, 7:3.

EXAMPLE 2

Stability of Liposomal Retinoic Acid

Liposomal $^3$H-retinoic acid (L-$^3$H-RA) was prepared with DMPC:DMPG, 7:3 as described in Example 1. Samples of the L-$^3$H-RA were incubated with either phosphate-buffered saline (PBS) or PBS with 20% (by volume) fetal calf serum (FCS). After various periods of incubation at about 37° C., aliquots were removed and centrifuged to sediment liposomes. The tritium in the supernatant solution was measured to determine $^3$H-RA release. FIG. 1 shows the release of $^3$H-RA over a two day period. The L-$^3$H-RA was over about 80 stable over the period of the experiment, even in the presence of 20% FCS.

When $^3$H-all-trans retinol was used to label L-ROH and stability in PBS measured, only about 5% of the $^3$H-ROH was released after a 24 hr incubation at 37° C.

EXAMPLE 3

In Vitro Lysis of Human Erythrocytes (RBCs) by Retinoic Acid or Liposomal Retinoic Acid Lysis of human red blood cells (RBCs) was quantitated by measuring the release of hemoglobin in the supernatants by observation of increases in optical density at 550 nanometers (nm), as described previously (Mehta, et al., Biochem. Biophys, Acta., Vol. 770-, pp 230–234 (1984). Free-RA dissolved in dimethyl formamide (DMFA), was added to the RBCs. Results with appropriate solvent controls, empty liposomes, and empty liposomes plus free-drug were also noted. Release of hemoglobin by hypotonic lysis of the same number of human RBCs by water was taken as a 100% positive control, while cells treated with PBS were taken as negative controls.

Preparations of L-RA comprising various lipids were incubated at a concentration of 20 microgram ($\mu$g) RA per ml with RBCs in PBS for 4 hr at 37° C. The toxicity of the L-RA preparations on the basis of percent RBC lysis is shown in Table 2.

TABLE 2

In Vitro Toxicity Of L-RA Preparations To RBCs

| LIPOSOME COMPOSITION | % RBC LYSIS |
| --- | --- |
| DMPC:Cholesterol 9:1 | 4.5 |
| DMPC:Cholesterol 9:3 | 90.2 |
| DPPC | 6.7 |
| DMPC:SA:Cholesterol 8:1:1 | 70.4 |
| DMPC:DMPG 7:3 | 8 |
| DMPC:DMPG 9:1 | 8.3 |

As may be seen from the data of Table 2, L-RA of DMPC:cholesterol, DPPC, DMPC:DMPG (7:3) and DMPC:DMPG (9:1) exhibited low RBC toxicity under these conditions. It is of interest to note that the latter two L-RA compositions exhibited superior encapsulation efficiencies (Table 1).

A further experiment concerning the toxicity over time of free RA and L-RA (DMPC:DMPG-7:3) toward RBC was conducted. Human erythrocytes were incubated at 37° C. in PBS with 10 $\mu$g/ml free RA or 120 ug/ml L-RA, and RBC lysis monitored over a period of 5 hr. FIG. 2 shows time courses of RBC lysis. At between about 1 hr and about 3 hr. the free RA extensively lysed a large majority of the erythrocytes. When a similar manipulation was performed with L-RA (DMPC:DMPG(7:3)) at a RA concentration of 120 ug/ml, little RBC lysis occurred (e.g., less than 10% after 6 hr).

Figure 3:
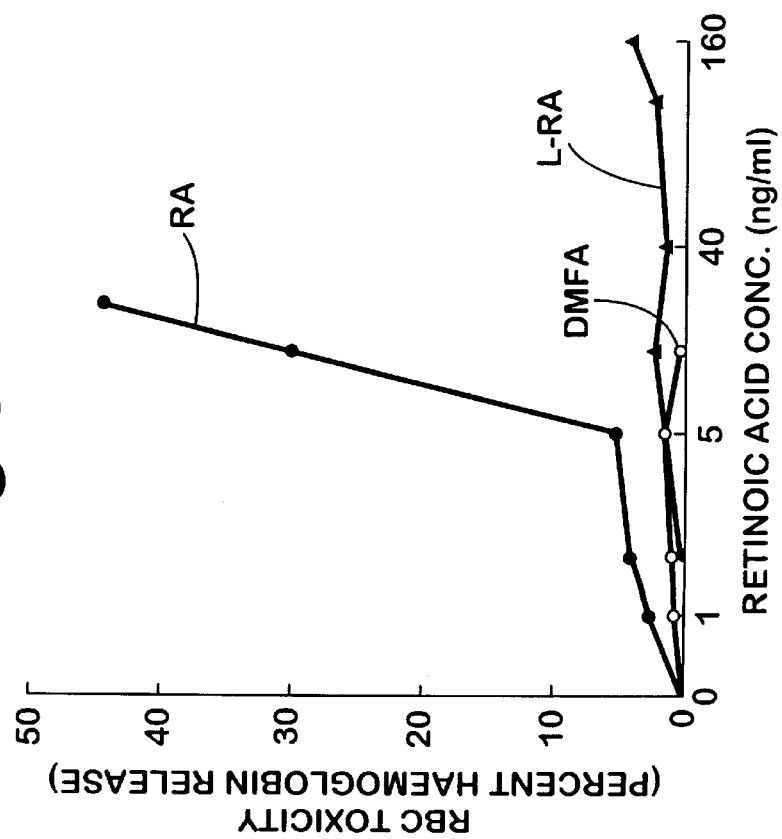
FIG. 3 shows RBC lysis as a function of retinoic acid (RA) concentration (●) and L-RA concentration (▲).

A study was also conducted concerning the effects upon RBC lysis in 2 hr of free RA and L-RA (DMPC:DMPG(7:3)) at various concentrations. FIG. 3 shows the results of this study. Free RA showed linearly increasing RBC lysis between about 5 ug RA/ml and about 30 ug RA/ml. Liposomal RA caused RBC lysis of only about 5% at a concentration of 160 ug RA/ml.

EXAMPLE 4

Acute Toxicity Of Free And Liposomal Retinoic Acid

The acute toxicity of free and liposomal all-trans retinoic acid was studied in CD1 mice. Free all-trans retinoic acid was prepared as an emulsion in normal saline containing 10% DMSO and 2% Tween 80 at a concentration of 3 to 5 mg/ml. Liposomal all-trans retinoic acid was prepared using a lipid:drug ratio of 15:1. The final concentration of all-trans retinoic acid in the liposomal preparation was 3 mg/ml. Empty liposomes of the same lipid composition (DMPC:DMPG 7:3) were also tested at doses equivalent to 80 mg/kg, 100 mg/kg, and 120 mg/kg of liposomal-all trans retinoic acid. Normal saline containing 10% DMSO and 2% Tween 80 was also tested as a control at a dose equivalent to 50 mg/kg of free all-trans retinoic acid. All drugs tested were injected intravenously via tail vein as a single bolus. The injected volumes of free and liposomal-all-trans retinoic acid were the same for each dose.

Table 3 shows data obtained from these acute toxicity experiments.

TABLE 3

Acute Toxicity of Free and Liposomal All-Trans Retinoic Acid

| Drug | Dose (mg/kg) | Number Animals with seizures | Number Animals alive (72 hr) |
| --- | --- | --- | --- |
| Free RA | 10 | 0/6 | 6/6 |
|  | 20 | 6/6 | 5/6 |
|  | 30 | 6/6 | 4/6 |
|  | 40 | 3/3 | 0/3 |
|  | 50 | 3/3 | 0/3 |
| L-RA | 40 | 0/6 | 6/6 |
|  | 60 | 0/6 | 6/6 |
|  | 80 | 0/6 | 6/6 |
|  | 100 | 0/6 | 6/6 |
|  | 120 | 0/6 | 6/6 |
| Empty Liposomes | 80 | 0/6 | 6/6 |
|  | 100 | 0/6 | 5/6 |
|  | 120 | 0/6 | 6/6 |
| Normal saline 10% DMSO 2% Tween 80 | 50 | 0/6 | 6/6 |

The maximum non-toxic dose of free all-trans retinoic acid was 10 mg/kg. Higher doses caused seizures immediately after injection. The acute $LD_{50}$ (deaths occurring up to 72 hours after injection) of free all-trans retinoic acid was 32 mg/kg. The cause of death was cardiopulmonary arrest after seizures for 1–2 minutes in all animals. No seizures or deaths were observed in the animals treated with liposomal all-trans retinoic acid at a dose of 120 mg/kg (maximum non-toxic dose and $LD_{50}$ greater than 120 mg/kg). Higher doses were not tested. No seizures were observed in the animals treated with empty liposomes or normal saline with 10% DMSO and 2% Tween 80.

EXAMPLE 5

In Vitro Inhibition of Tumor Cell Growth

Liposomal all-trans retinoic acid (L-RA) was prepared as described in Example 1.

Cells of the human monocytic cell line THP-1 were inoculated into samples of eucaryotic cell culture medium in the presence or absence of L-RA, at a final RA concentration of 1 micromolar ($\mu$m). After 24 hr at 37° C., $^3$H-thymidine was added to each culture and incorporation thereof into cellular polynucleotides measured. Table 4 shows the percentage of tumor growth inhibition as reflected by decreases in $^3$H-thymidine incorporation induced by L-RA of differing lipid compositions.

TABLE 4

L-RA Inhibition of Tumor Cell Growth

| LIPOSOME COMPOSITION | TUMOR CELL (THP-1) INHIBITION (%) |
|---|---|
| DMPC:Cholesterol 9:1 | 72 |
| DMPC:Cholesterol 9:3 | 22 |
| DPPC | 8 |
| DMPC:SA:Cholesterol 8:1:1 | 84 |
| DMPC:DMPG 7:3 | 70 |
| DMPC:DMPG 9:1 | 32 |

From Table 4, it should be noted that L-RA (DMPC:DMPG-7:3), which, as previously shown herein, gave a superior encapsulation efficiency and showed a low RBC toxicity (Tables 1 and 2), also effectively inhibited the tumor cell growth.

Cells of the human monocytic cell line THP-1 and of the human histiocytic cell line U-937 were inoculated at about 20,000 cells per cell in aliquots of eucaryotic cell culture medium contained in wells of a 96 well microtiter plate. The medium in various wells contained different amount of free RA or L-RA (DMPC:DMPG 7:3). The cells were incubated for 72 hr at 37° C. and cell growth determined and compared to that of controls without any form of retinoic acid. FIG. 4 shows the inhibition of THP-1 cell growth by increasing concentrations of free RA or L-RA (DMPC:DMPG 7:3). At concentrations of less than 1 µg RA/ml, both preparations inhibited cell growth by over 90%.

The human monocytic leukemia THP-1 cells, after a 72 hr incubation with either free RA or L-RA at a concentration of 0.3 µg RA/ml, were observed to have lost their generally ovate form and to have a more flattened and spread morphological appearance often associated with cellular differentiation. The generally ovate form was retained when the cells were cultured in the absence of any free or liposomal retinoic acid.

Figure 5:
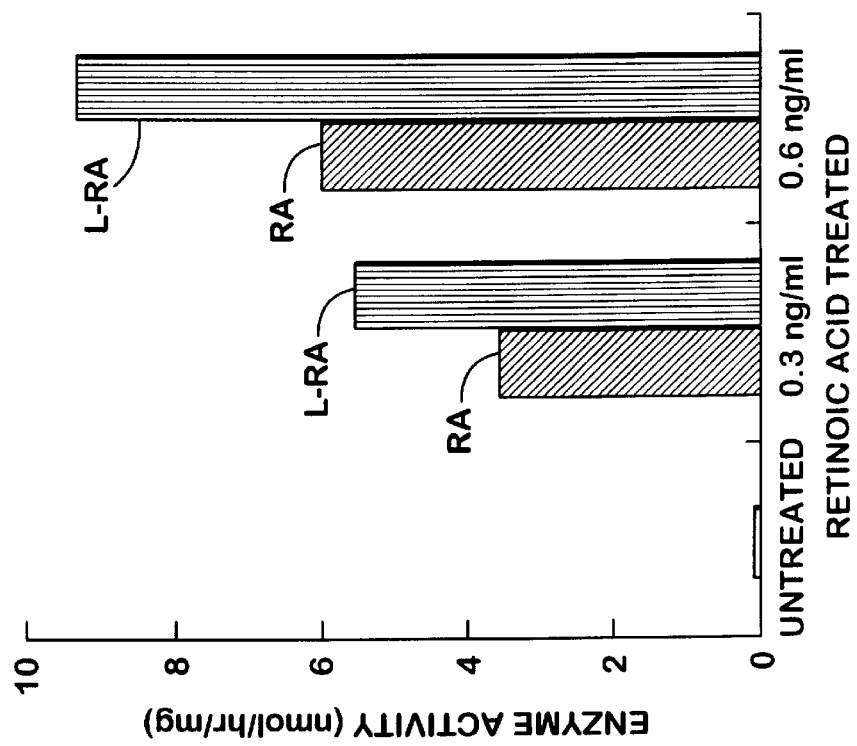
FIG. 5 shows the induction of transglutaminase (TGase) in human monocytic THP-1 cells as a function of treatment with RA or L-RA.

After incubation for 24 hr with 0.3 µg/ml or 0.6 µg/ml RA or L-RA in another experiment, THP-1 cells had increased levels of tissue transglutaminase enzymic activity, a marker for monocytic cell differentiation. As shown in FIG. 5, THP-1 cells, at $4 \times 10^5$ cells/ml, showed about 50% greater transglutaminase activity when incubated with L-RA as compared to free RA at equivalent retinoic acid concentrations.

Figure 6:
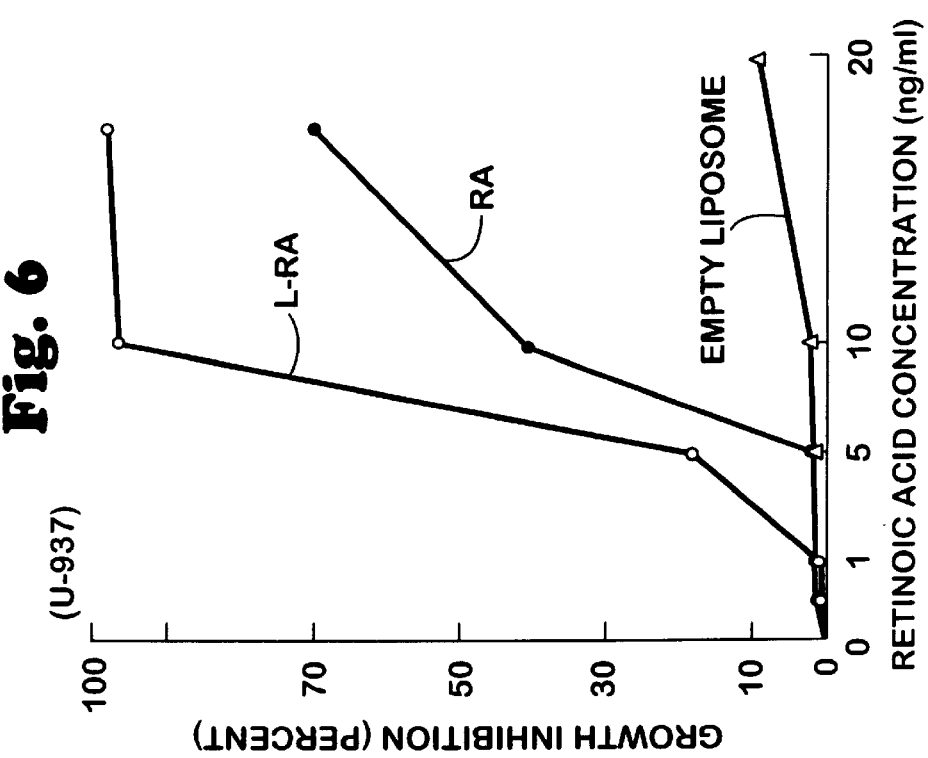
FIG. 6 shows the inhibition of human histiocytic U-937 cell growth as a function of RA concentration (●), L-RA concentration (O) and empty liposome concentration (Δ).

Cells of the human histiocytic cell line U-937 were distributed and cultured under the same conditions as the THP-1 cells in the prior experiment. FIG. 6 shows the effects upon cell growth of increasing concentrations of free all-trans retinoic acid (RA), liposomal (DMPC:DMPG 7:3) all-trans retinoic acid (L-RA) and empty liposomes (which were devoid of retinoic acid). It should be noted that the U-937 cells were almost completely growth-inhibited by L-RA at a retinoic acid concentration of about 10 ug/ml while this amount of free RA inhibited growth less than 50%.

EXAMPLE 6

Antitumor Activity of Liposomal All-Trans Retinoic Acid in Vivo

The antitumor activity of liposomal-all trans retinoic acid (DMPC:DMPG 7:3) was tested in vivo against liver metastases of M5076 reticulosarcoma. C57BL/6 mice were inoculated with 20,000 M5076 cells on day 0. Intravenous treatment with 60 mg/kg liposomal all-trans retinoic acid was given on day 4. The mean survival of control animals (non-treated) was 21.8+1.6 days. The mean survival of treated animals was 27.0±1.6 days. Liposomal all-trans retinoic acid was shown, therefore, to have antitumor activity at a dose well below the maximum non-toxic dose, against a cell line (M5076) which was resistant to free retinoic acid in in vitro studies. THP-1 cells treated in vitro with RA (1 MM) for 72 hours when injected subcutaneously into male mice, failed to develop into tumors, whereas untreated cells formed a huge mass of tumors in such mice.

EXAMPLE 7

Induction of Tissue Transglutaminase in Human Peripheral Blood Monocytes by Intracellular Delivery of Retinoids Circulating blood monocytes are the precursors of macrophages which accumulate at the sites of tumor rejection [2], delayed hypersensitivity [25], chronic inflammation [6], and at the site of damaged tissue as a part of the healing processes [11] (see reference citations in section D). At these sites, peripheral blood monocytes acquire new functional and biochemical characteristics that are associated with the maturation or differentiation process. To understand clearly the mechanisms involved in differentiation, it is necessary to manipulate the extracellular environment and assess precisely a variety of cellular functions and biochemical activities.

Vitamin A and its analogues (retinoids) have been shown to exert a profound effect on the differentiation of monocytic cells. Both normal [19] and leukemic [7,17,28] monocytic cells differentiate in response to retinoids which might suggest that retinoids play a role in regulating the differentiation of these cells. According to recent reports, the cellular activity of transglutaminase (TGase), an enzyme that catalyzes the covalent cross-linking of proteins, may be directly linked to the retinoid's action [4,15,21,23,35,39,39]. Recently, the present inventors found that in vitro maturation of human peripheral blood monocytes (HPBM) to macrophage-like cells was associated with the induction and accumulation of a specific intracellular TGase, tissue TGase [19,22]. Gamma (g)-interferon, which promotes the tumoricidal properties in HPBM, also augmented the expression of tissue TGase [19]. Similarly, the activation of guinea pig and mouse macrophages in vivo was associated with a marked increase in tissue TGase activity [10,24,34]. Terminal differentiation of human monocytic leukemia cells (THP-1) induced by phorbol ester and retinoic acid was associated with induction and accumulation of tissue TGase [17], suggesting that the induction of tissue TGase was a marker of monocytic cell differentiation. The present invention involves further definition of the role of retinoids in differentiation and maturation of HPBM and comprises studies of culture conditions that inhibit or facilitate the internalization of retinoids by HPBM on expression of tissue TGase. The studies herein demonstrate that HPBM, isolated into two subpopulations, show no significant difference in their ability to express tissue TGase activity induced by either in vitro culture or exposure to recombinant interferon gamma (rIFN-g), and that the expression of tissue TGase in cultured HPBM may be induced by a direct delivery of retinoids to intracellular sites.

A. Materials and Methods

1. Materials

RPMI-1640 medium supplemented with L-glutamine and human AB serum were from Gibco Laboratories (Grand Island, N.Y.); *Escherichia coli*-derived human recombinant g-interferon (rIFN-g) was kindly supplied by Genentech Inc. (South San Francisco, Calif.); and all-trans retinol (ROH) and all-trans retinoic acid (RA) were purchased from Sigma Chemical Co. (St. Louis, Mo.). The chromatographically pure lipids dimyristoyl phosphatidyl choline (DMPC) and dimyristoyl phosphatidyl glycerol (DMPG) were from Avanti Polar Lipids (Birmingham, Ala.); tritiated putrescine (sp. act. 28.8 Ci/mmol), from New England Nuclear (Boston, Mass.); and tritiated ROH (sp. act. 15 mci/mmol), from Amersham (Arlington Heights, Ill.). Lipids, culture medium, and serum were screened for endotoxin with the Limulus amebocyte lysate assay (MA Bioproducts, Walkersville, Md.), and they were used only when endotoxin contamination was less than 0.25 ng/ml.

2. HPBM Isolation, Purification, and Culture

Pure populations of HPBM were obtained by countercurrent centrifugal elutriation of mononuclear leukocyte-rich fractions obtained from normal donors who were undergoing routine plateletpheresis [12]. HPBM were isolated into two subpopulations according to size with a Coulter ZBI counter and C-1000 channelizer (Coulter Electronics, Hialeah, Fla.). The median volume of small monocytes was 255 $mm^3$, and that of the large monocytes was 280 $mm^3$. The small monocytes were 95%±3% nonspecific esterase-positive and the large monocytes were 98%±2% positive. Detailed procedures for isolation and characteristics of these subpopulations have been published elsewhere [36,37]. Small, large, or mixed (obtained by mixing equal parts of small and large HPBM) HPBM subpopulations were washed once with medium (RPMI-1640 supplemented with L-glutamine, 20 mM HEPES buffer, 20 ug/ml gentamicin, and 5% human AB Serum) and resuspended to 0.5 million/ml density in the same medium. The cells were dispensed in 4-ml samples into 35-mm-well plates and cultured under appropriate conditions.

3. Enzyme Assay

Tissue TGase activity in cell extracts was measured as a $Ca^{2+}$, dependent incorporation of [$^3$H] putrescine into dimethylcasein. In brief, cultured HPBM were washed three times in Tris-buffered saline (20 mM Tris-HCl, 0.15 M NaCl, pH 7.6) and scraped from the dish in a minimal volume of the same buffer containing 1 mM EDTA and 15 mM Beta-mercaptoethanol. The cells were lysed by sonication, and TGase activity in the lysates was determined as described previously [13,20]. The protein content in cell lysates was determined by Lowry's method [14] with bovine gamma globulin as standard. The enzyme activity was expressed as nanomoles of putrescine incorporated into dimethyl-casein per hour per milligram of cell protein.

4. Immunochemical Detection of Tissue TGase

To detect tissue TGase in cell extracts, the cell lysates were solubilized in 20 mm Tris-HCl (pH 6.8) containing 1% sodium dodecyl sulfate (SDS), 0.75 M Beta-mercaptoethanol, 2.5% sucrose and 0.001% bromophenol blue. Solubilized extracts were fractionated by electrophoresis on a 6.5% discontinuous polyacrylamide gel and electroblotted onto nitrocellulose paper. The paper was neutralized with 5% bovine serum albumin and treated with iodinated anti-tissue TGase antibody; the preparation, characterization and properties of this antibody have been described elsewhere [24]. The unbound antibody was removed by washing the paper in Tris-HCl buffer (50 mM, pH 7.5) containing 200 mM NaCl, 5 mM EDTA, 0.5% Triton X-100, 0.1% SDS, and 0.25% gelatin, and the paper was dried and autoradiographed as described earlier [20,24].

5. Preparation of Liposomes

Multilamellar vesicles (liposomes) containing DMPC and DMPG at a molar ratio of 7:3 were prepared as described [16,18]. All-trans ROH or RA were encapsulated by adding the required amount of the drug (predissolved in ethanol) in lipid-containing organic solvents before vacuum drying. The dried lipid-drug film was dispersed by agitation in sterile saline solution. Retinoids up to a 1:10 drug:lipid ratio could be completely encapsulated within the liposomes and were highly stable. The stability and encapsulation efficiency of the liposome preparations were studied by using radiolabeled retinol and showed that only 5%±2% of the incorporated radioactivity leaked out in the supernatant after 24-hr incubation at 37° C.

6. Binding Assay for [$^3$H] ROH

Freshly isolated HPBM were cultured in serum containing medium alone or medium plus 50 units (U)/ml rIFN-g for varying periods of time. At the end of indicated time periods, HPBM monolayers were washed twice in ice cold medium and resuspended in 0.5 ml of prechilled reaction mixture containing 5.0 microcuries ($\mu$Ci)/ml [11,12(n)$^3$H] vitamin A (free ROH) in RPMI medium supplemented with 5% delipidized human AB serum (serum delipidization was done by organic solvent extraction as described earlier [33]. Binding assays were carried out for 1 hr in an ice bath. After a 1-hr incubation, the monocyte monolayers were washed six times with ice-cold medium and the cells were lysed in 200 $\mu$l of Triton X-100. Fifty-microliter aliquots of cell lysates, in triplicate, were counted for the cell-associated radioactivity. Background counts, obtained by adding the reaction mixture toward the end of the 1-hr incubation before harvesting, were subtracted from the experimental values.

B. Results

1. Tissue TGase Induction During In Vitro Culture of HPBM

Figure 7:
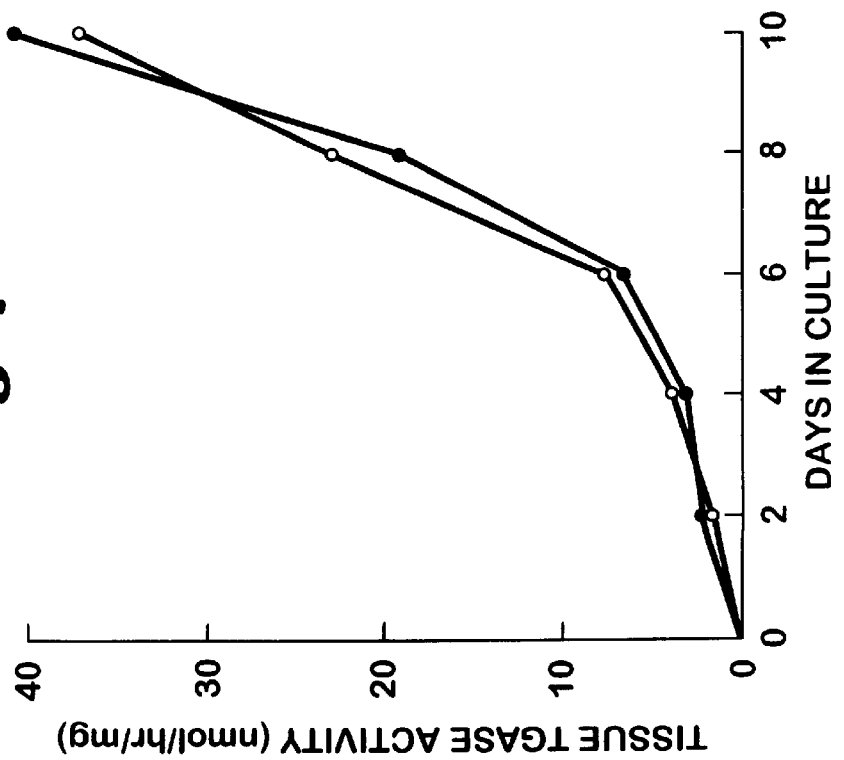
FIG. 7 shows the time course of accumulation of tissue TGase activity in cultured human peripheral blood monocytes (HPBM). HPBM were fractionated into small (O) and large (●) subpopulations by centrifugal elutriation, and they were cultured in 35-mm-well tissue culture plates as described in Materials and Methods. At the indicated time points the cells were washed, sonicated, and assayed for TGase activity. Values are the means of six determinations from two dishes.

The culture of HPBM in the presence of serum-containing medium for up to 10 days was associated with a marked induction of tissue TGase activity in both small and large HPBM (FIG. 7), the increase in enzyme activity being more rapid after about 4 days of culture. After 10 days in culture, small monocytes showed a 93-fold increase in enzyme activity (from 0.44 to 41.1 nmol/hr/mg), whereas large HPBM accumulated about 103-fold increase in the enzyme activity (from 0.36 to 37.4 nmol/hr/mg). Small and large HPBM mixed together and cultured under similar conditions showed no significant difference in the rate and amount of accumulation of tissue TGase activity compared with that of individual HPBM fractions (data not shown). Induction of enzyme activity was associated with a change in the morphology of cultured monocytes. Freshly isolated HPBM looked rounded, but after 6–8 days in culture both the large and small HPBM became firmly adherent to the plastic surface, were more spread and flattened, and had the appearance typical of mature macrophages. By day 10, when the cells had accumulated maximal levels of enzyme activity, these levels then either plateaued or started declining.

2. Effect of rIFN-g on Tissue TGase Expression

Figure 8:
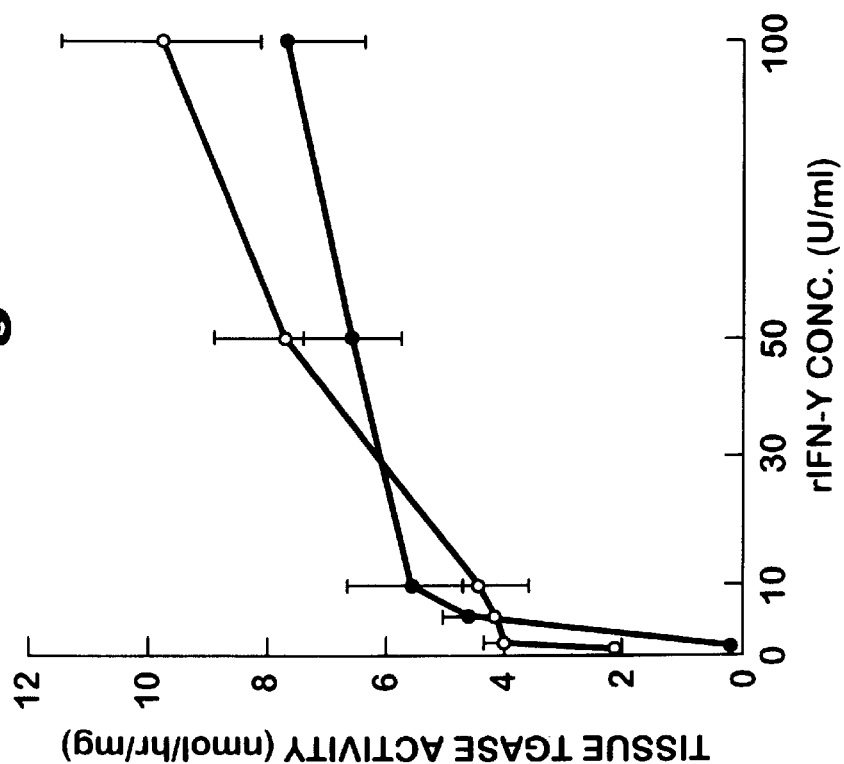
FIG. 8 shows dose-dependent effects of recombinant interferon-gamma (rIFN-g) on induction of tissue TGase activity in HPBM subpopulations. Small (O) and large (●) monocytes were cultured in serum containing medium alone or medium containing increasing concentrations of rIFN-g. After 72 hr, the cells were harvested and the cell lysates assayed for tissue TGase activity. The results shown represent mean±SD of three determinations from an individual donor.

The effect of continuous exposure to rIFN-g on induction of tissue TGase activity in HPBM is shown in FIG. 8. Small and large monocytes were cultured in serum-containing medium for 72 hr in the presence of increasing concentrations of rIFN-g. Enzyme activity in the HPBM populations increased significantly after their continuous exposure to rIFN-g compared with that of cells cultured in the presence of medium along. However, rIFN-g dose size produced no significant difference in enzyme activity between the two HPBM populations. As previously noted [19], a 100-U/ml dose of rIFN-g seemed to be optimal for augmenting TGase activity; higher rIFN-g-concentrations were less effective. The inductive effect of rIFN-g on tissue TGase activity was evidence at 5 U/ml and pretreatment of HPBM cultures with rIFN-g (100 U/ml) followed by washing and subsequent culture in medium alone did not enhance the expression of tissue TGase. The rIFN-g-induced augmentation of tissue TGase was associated with morphologic changes in HPBM so that the rIFN-g-treated cells were more spread out and flattened than the untreated control cells after three days in culture.

3. Effect of Retinoids on Tissue TGase Induction

Figure 9B:
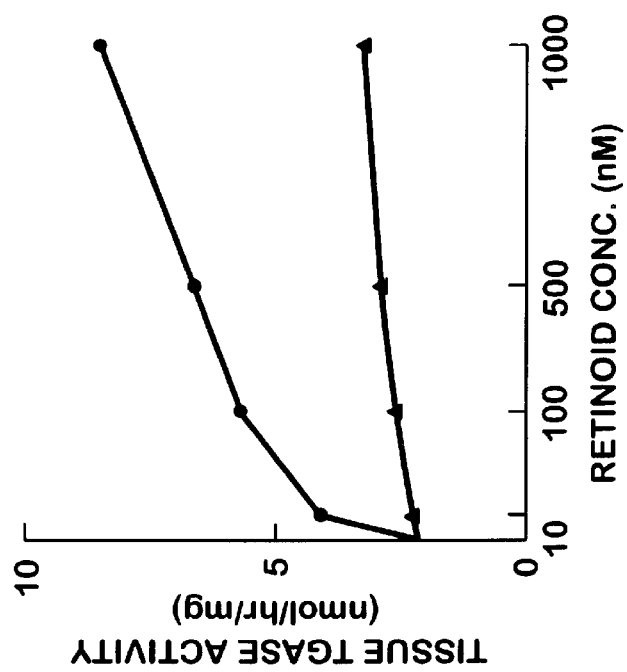
FIG. 9 shows effects of retinol (ROH) and RA on induction of tissue TGase activity in cultured HPBM. Cells were cultured in the presence of 5% human AB serum and the absence (O) or presence of 500 nM ROH (▲) or RA (●) for varying periods of time. At the end of each time point, the cells were harvested and assayed for enzyme activity. Values shown are the means±SD of six determinations from two independent experiments. Inset, dose-response curve for tissue TGase induction by ROH (▲) and RA (●) in HPBM after 72-hr culture.
Figure 9A:
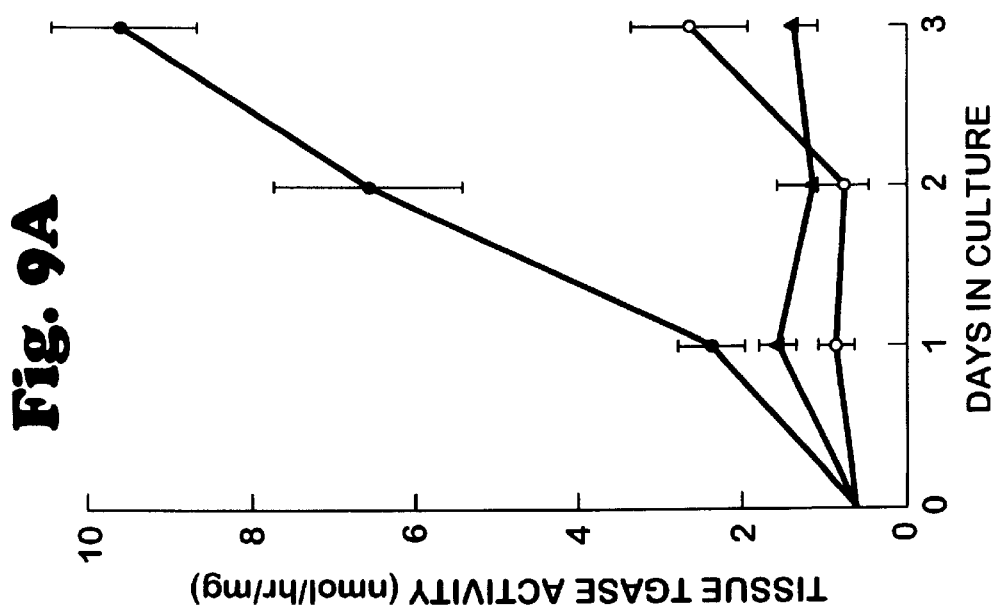

Since the two HPBM populations showed no heterogeneity in terms of induced tissue TGase levels, our subsequent studies were done with whole HPBM fraction without separation into subsets. HPBM cultured in the presence of 500 nM RA for 24 hr accumulated at least three-fold higher enzyme activity than did the control cells cultured in medium along (FIG. 9). Continuous exposure to RA caused a rapid and linear increase in the enzyme activity, whereas in the control cells no significant change in the level of tissue TGase activity was observed for up to 2 days of culture. By day 3, the control cells accumulated about six-fold higher enzyme activity (3.4 nmol/hr/mg) than did freshly isolated HPBM (0.6 nmol/hr/mg), but they still had significantly less enzyme activity than the RA-treated cells (9.8 nmol/hr/mg). Retinoic acid-induced expression of tissue TGase was dose dependent (FIG. 9 inset). ROH, the physiologic analogue of RA, did not induce the expression of tissue TGase in HPBM even at a dose of 1 $\mu$M. Thus, HPBM cultured in the presence of ROH for up to 3 days showed no significant difference in accumulation of tissue TGase activity when compared with that of control cells cultured in medium along (FIG. 9).

4. Effect of Liposome-Encapsulated Retinoids on Tissue TGase Induction

Figure 10A:
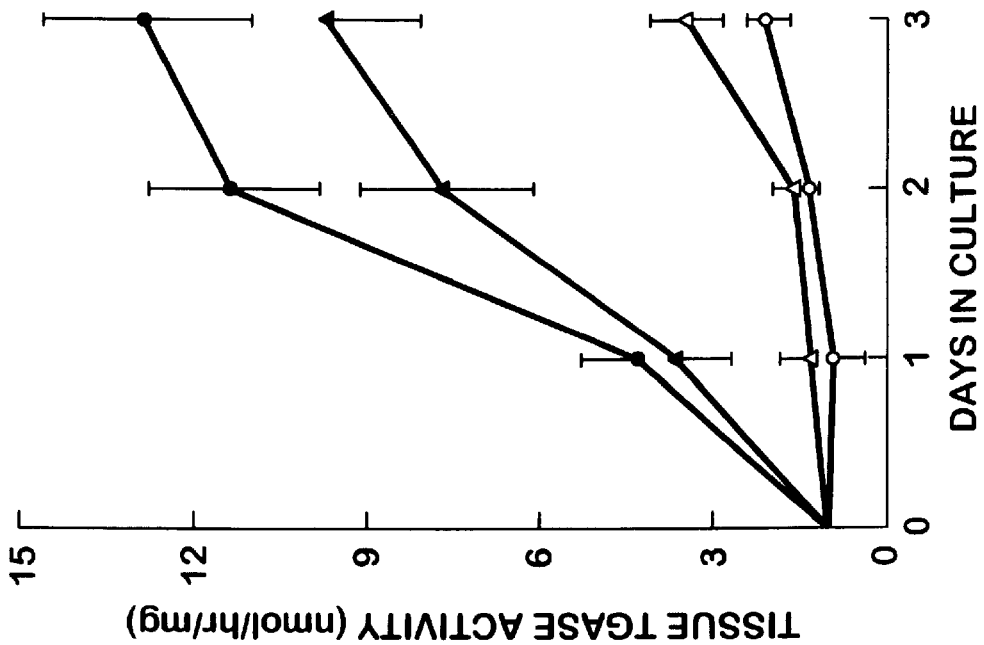
FIG. 10 shows effects of free- and liposome-encapsulated RA on induction of tissue TGase in HPBM. A: The cells were cultured in tissue culture dishes in presence of serum-containing medium alone (Δ) 500 nm liposomal RA (●), or medium containing 500 nM free-RA (▲), or "empty liposomes" (O) for indicated periods of time. Both the liposomal RA and "empty liposomes" contained 200 μg/ml lipid. At the end of each time point, the cultures were washed and cell lysates assayed for TGase activity. Values shown are the mean±SD of six determinations from two independent experiments. B: Western-blot analysis of the levels of tissue TGase in freshly isolated HPBM (lane 1) and in HPBM cultured for 72 hr in the presence of serum-containing medium alone (lane 2), in medium containing 500 nM free RA (lane 3), 500 nM liposomal RA (lane 4), or "empty liposomes" (lane 5). Cell lysates containing 25 ug of protein were subjected to Western-blot analysis as described in Materials and Methods.
Figure 10B:
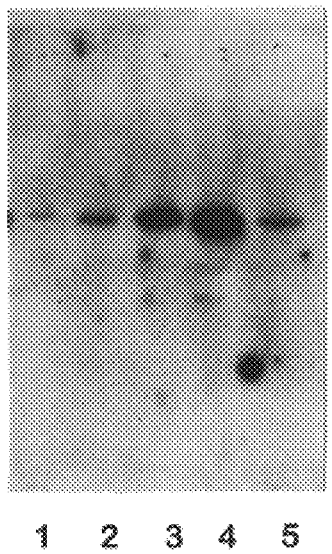

Liposome-encapsulated RA was more effective in inducing tissue TGase expression than was free RA at an equimolar concentration. After 24-hr culture, the amount of tissue TGase activity in HPBM induced by free or liposomal RA at an equimolar concentration of 500 nM was not significantly different (3.4 and 3.7 nmol/hr/mg, respectively); after 48 and 72 hr, however, liposomal RA-treated cells accumulated at least 50% more enzyme activity than did free RA-treated cells (FIG. 10A). That increase in enzyme activity by liposome-encapsulated RA was a specific effect of RA and not of lipids was demonstrated by the fact that a culture of HPBM in the presence of "empty liposomes," and containing equivalent amount of lipids did not induce enzyme activity throughout the incubation period. "Empty liposomes," as reported earlier [20], inhibited serum-induced expression of tissue TGase after 72 hr of culture (FIG. 10A) . The free or liposomal RA-induced increase in enzyme activity was caused by an increased amount of the enzyme peptide, as revealed by Western-blot analysis of cell lysates using a iodinated antibody to tissue TGase (FIG. 10B). The increase in enzyme activity was proportional to the increase in enzyme peptide and not caused by activation of preexisting enzyme.

Figure 11A:
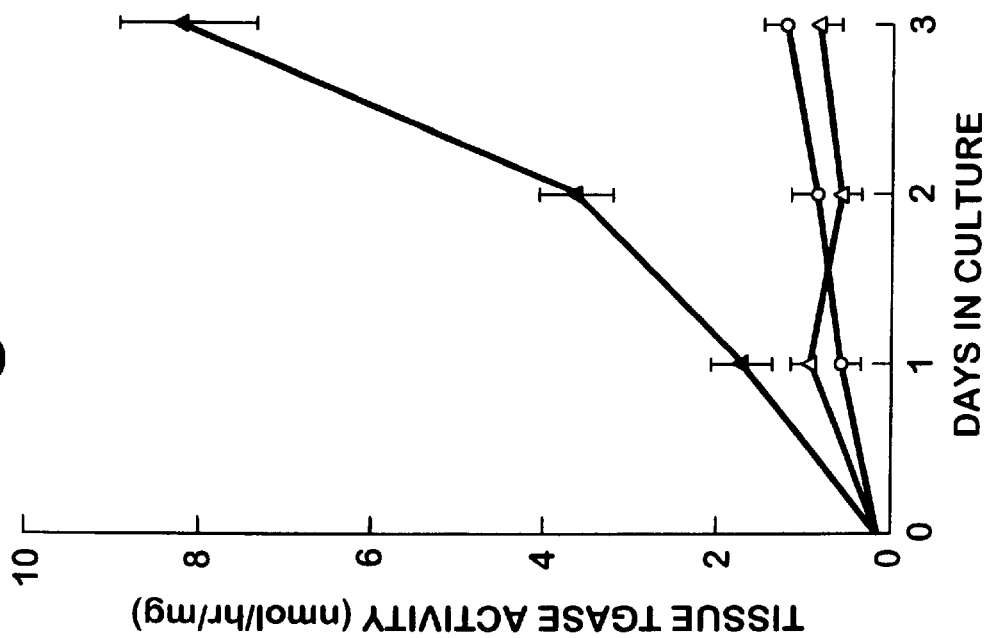
FIG. 11 shows effect of free and liposome-encapsulated ROH on induction of tissue TGase in HPBM. A: HPBM monolayers were cultured in serum-containing medium alone (Δ) or medium containing 1 μM of free- (O) or liposomal-ROH (▲) for 72 hr. Then the cultures were washed and the cell lysates assayed for enzyme activity as described in Materials and Methods. B: Western-blot analysis of tissue TGase levels in freshly isolated HPBM (lane 1) and in HPBM cultured for 72 hr in the presence of serum-containing medium alone (lane 2), in medium containing 1 μM of free ROH (lane 3), or liposome-encapsulated ROH (lane 4) as described in Materials and Methods. Twenty-five micrograms of cell protein was loaded onto each lane.
Figure 11B:
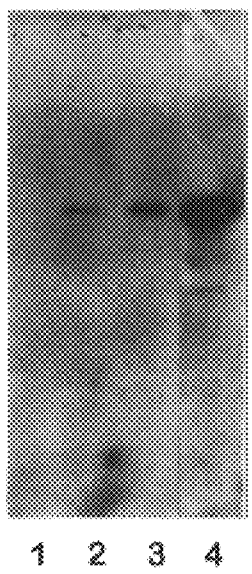

Retinol, which in its free form was unable to enhance the expression of tissue TGase in HPBM, became active when presented in liposomal form. Liposome-encapsulated ROH caused a rapid and linear increase in tissue TGase activity with time in culture (FIG. 11A). After 72 hr of culture, liposomal-ROH caused a nine-fold increase in enzyme activity (7.1 nmol/hr/mg) when compared to that of control cells exposed to free ROH under similar conditions (0.8 nmol/hr/mg). Liposomal ROH-induced expression of tissue TGase resulted from increased accumulation of the enzyme peptide as demonstrated by Western-blot analysis (FIG. 11B).

5. Tissue TGase induction is Related to HPBM Uptake of Retinoids

The effect of in vitro maturation and rIFN-g treatment on the binding of tritiated-ROH by HPBM was examined. After 4 days of control culture (medium dose), tritiated-ROH binding by HPBM increased 50% compared to this binding by freshly isolated cells. After 9 days the control culture binding value increased to 350%. The increases in ROH binding were associated with parallel increases in tissue TGase activity (Table 5).

TABLE 5

Effect of In Vitro Culture and rIFN-g Treatment on [$^3$H]ROH Binding by HPBM

| Culture Conditions | Days in Culture | [$^3$H]ROH bound (cpm/10 $\mu$g protein) | Tissue TGase activity (nmol/hr/mg) |
|---|---|---|---|
| medium alone | 0 | 684 ± 25 | 0.25 ± 0.13 |
|  | 4 | 994 ± 115 | 2.96 ± 0.75 |
|  | 9 | 2,220 ± 144 | 32.60 ± 8.50 |
| medium alone | 3 | 626 ± 37 | 2.9 ± 0.23 |
| medium + rIFN-g | 3 | 1,782 ± 130 | 7.6 ± 0.7 |

[a]HPBM were cultured in serum-containing medium alone or medium containing 50 U/ml rIFN-g for indicated periods of time.
[b]Binding of tritiated ROH during different periods of culture was determined as described in Materials and Methods.
[c]Parallel cultures of HPBM maintained under similar conditions were used for assaying enzyme activity as described in Materials and Methods.

Exposure of HPBM to rIFN-g augmented the ROH binding and the expression of enzyme activity. The rIFN-g-treated cells showed a threefold higher [$^3$H]ROH binding than did control cells incubated in the presence of serum-containing medium alone for the same period of time. The presence of delipidized serum in the reaction mixture was essential; only 10% of the total counts were cell-associated when delipidized serum was omitted from the reaction mixture.

C. Discussion

The results reported in this Example suggested that HPBM, isolated into two populations based on their size and density, have equal potential to differentiate into mature macrophages. The in vitro maturation of HPBM to macrophages was associated with enhanced binding and uptake of retinol, presumably as a result of the acquisition of cell surface receptors for serum retinol-binding protein. Exposure of HPBM to rIFN-g for 72 hr led to enhanced binding of [$^3$H]ROH that was comparable to the binding activity of control HPBM cultured in vitro for 9 days. HPBM maturation induced by in vitro culture or by exposure to rIFN-g was accompanied by similar morphologic and enzymatic changes. The requirement of cell surface receptor for serum retinol-binding protein could be circumvented by direct intracellular delivery of ROH.

Recently, several reports have suggested an association between monocytic cell differentiation and induction of tissue TGase [10,17,19,21–24,34]. Freshly isolated HPBM that have very low levels of tissue TGase accumulate large amounts of this enzyme after their in vitro maturation [19,22]. Just as the two subpopulations of HPBM showed no significant difference in their ability to induce and accumulate tissue TGase activity during in vitro differentiation to macrophages, both fractions were equally responsive to the effect of rIFN-g in terms of augmented enzyme expression (FIG. 8). Functional heterogeneity among HPBM subpopulations isolated by similar criteria has been reported earlier. Thus, the subsets of HPBM isolated into small and large populations have been reported to produce different amounts of reactive oxygen species [37], prostaglandins [1,30], antibody dependent cell-medicated cytotoxicity [27], and tumor-cell killing [26]. This functional heterogeneity among HPBM subpopulations has been attributed to either maturational or clonal differences. The data presented herein, however, suggest no heterogeneity among HPBM subpopulations in induction of tissue TGase, a marker for monocytic cell differentiation, and equal potential for differentiating into mature macrophages. The ability of rIFN-g to enhance tissue TGase expression in both HPBM subpopulations suggests that this endogenous cytokine may play an important role in the maturation, differentiation, and expression of differentiated functions in monocytic cells.

The factors in serum responsible for induction and accumulation of tissue TGase in cultured HPBM and macrophages have been shown to be endogenous retinoids and serum retinol-binding protein [21]. Extraction of retinoids by delipidization or depletion of retinol-binding protein from the serum completely abolished its enzyme-inducing ability [19,21]. Serum retinol-binding protein is believed to be responsible for intravascular transport and delivery of retinol to specific target tissues [8,9,29,31]. Receptors for serum retinol-binding protein present on the surface of target cells are responsible for the specificity of the delivery process [9,31]. The binding of ROH-retinol-binding protein complex to cell surface receptors apparently facilitates the delivery of ROH into the interior of the cell [9,31]. At superphysiologic doses (greater than 10 nM) on the other hand, RA can enter the cells directly by simple diffusion without the participation of surface receptors for retinol-binding protein [21]. This suggested that freshly isolated HPBM probably lack the cell surface receptors for serum retinol-binding protein and therefore cannot internalize the endogenous or exogenous retinoids. Indeed, the addition of exogenous RA to HPBM cultures at doses (e.g. greater than 10 nM) at which the receptor-mediated delivery becomes irrelevant resulted in a marked induction of tissue TGase activity (FIG. 9). The enzyme-inducing ability of RA was augmented further by encapsulating RA within the liposomes and allowing its internalization via phagocytosis (FIG. 10).

Of particular interest was the effect of ROH, which, in its free form did not induce the expression of tissue TGase in freshly isolated HPBM. When ROH was encapsulated within liposomes, however, the requirement for a cell surface receptor for serum retinol-binding protein was obviated. Thus liposomal ROH induced a significant level of tissue TGase activity in HPBM (FIG. 11). This suggested an effective approach for targeting retinol or its inactive analogues to the monocytic cells with no or minimal toxic effects. Because HPBM lack cell surface receptors for serum retinol-binding protein makes administered ROH subject to nonspecific internalization by other cell types. The present studies suggested, furthermore, that interaction of ROH-retinol binding-protein complex with the cell surface receptor is required only for the intracellular delivery of retinol and that, unlike in the case of other hormones [3], ligand-receptor interaction may not require a second messenger for expression of the final event. The increase in TGase enzyme activity induced by free RA or liposome-encapsulated RA or ROH, was the result of the accumulation of enzyme protein rather than the activation of preexisting enzyme, as revealed by immunoblots of the cell lysates using an iodinated antibody to tissue TGase (FIGS. 10,11).

Preliminary data on tritiated ROH-binding (Table 5) further supported the concept that in vitro differentiation of HPBM to mature macrophages was associated with acquisition of cell surface receptors for retinol-binding protein and that treatment with rIFN-g augmented the expression of these receptors. Once the HPBM acquire these receptors, they could internalize the endogenous retinoids and induce the expression of tissue TGase. Indeed, retinoids have been shown specifically to trigger the gene for tissue TGase in myelocytic cells [23].

Impairment of macrophage function in retinoid-deficient animals has been well documented to lead to increased incidence of infections and decreased tumor-cell killing [5]. In cultures of guinea pig peritoneal macrophages, RA has been reported to increase the intracellular levels for the tumoricidal enzyme arginase [32]. The present findings that retinoids play an important role in the differentiation process of HPBM support the idea that retinoids are the important regulators of monocyte/macrophage functions.

D. REFERENCES

1. Bankhurst, A. D., Hastein, E., Goodwin, J. S., and Peake, J. E. The nature of the prostaglandin-producing mononuclear cells in human peripheral blood. J. Lab. Clin. Med. 97, 179, 1981.
2. Baum, M., and Fisher, S. Macropnage production by bone marrow of tumor bearing mice. Cancer Res. 32, 2813, 1972.
3. Cuatrecasas, P. Hormone receptors, membrane phospholipids and protein kinases. Harvey Lect. 80, 89, 1986.
4. Davies, P. J. A., Murtaugh, M. P., Moore, W. T., Johnson, G. S., and Lucas, D. S. Retinoic acid-induced expression of tissue transglutaminase in human promyelocytic leukemia (HL-60) cells, J. Biol. Chem. 260, 5116, 1985.
5. Dennert, G. Retinoids and the immune system; Immunostimulation by vitamin A. In the Retinoids, Vol. 2 (Sporn, M. B., Roberts, A. B., and Goodman, D. S., Eds.) New York: Academic Press, p. 373, 1984.
6. Dizon, Q. S., and Southam, C. M. Abnormal cellular response to skin abrasions in cancer patients. Cancer 16, 1288, 1963.
7. Ferrero, D., Pressano, S., Pagliardi, G. L., and Robera. G. Induction of differentiation of human myeloid leukemias: surface changes probed with monoclonal antibodies. Blood 61, 171, 1983.
8. Ganguly, J., Roa, M. R. S., Murthy, S. K., and Sarada, K. Systemic mode of action of vitamin A. Vitam. Horm. 38, 1, 1980.
9. Heller J. Interaction of plasma retinol-binding protein with its receptors: specific binding of bovine and human retinol-binding proteins to pigment epithelium cells from bovine eyes. J. Biol. Chem. 248, 3613, 4975.
10. Leu, R. W., Herriot, M. J., Moore, P. E., Orr, G. R., and Birckbichler, P. J. Enhanced transglutaminase activity associated with macrophage activation. Exp. Cell Res. 141, 191, 1982.
11. Liebovich, S. J., and Ross, R. The role of the macrophage in wound repair. A study with hydrocortisone and antimacrophage serum. Am. J. Pathol. 78, 71, 1975.

12. Lopez-Berestein, G., Reuben, J., Hersh, E. M., Kilbourn, R., Hester, J. P., Bielski, M., Talpaz, M., and Mavligit, G. M. Comparative functional analysis of lymphocytes and monocytes from plateletpheresis. Transfusion 23, 201, 1983.

13. Lorand, L., Rule, N. G., Ong, H. G., Furlanetto, R., Jacobsen, A., Downey, J., Over, N., and Lorand, J. Amine specificity in transpeptidation. Inhibition of fibrin cross-linking. Biochemistry 7, 1214, 1980.

14. Lowry, O. H., Rosebrough, N. J., Farr, A. L., and Randall, R. J. Protein measurement with folin-phenol reagent. J. Biol. Chem. 193, 265, 1951.

15. Mehta, K., Claringbold, P., and Lopez-Berestein, G. Amphotericin B. inhibits the serum-induced expression of tissue transglutaminase in murine peritoneal macrophages. J. Immunol. 136, 4306, 1986.

16. Mehta, K., Juliano, R. L., and Lopez-Berestein, G. Stimulation of macrophage protease secretion via liposomal delivery of muramyl dipeptide derivatives to intracellular sites. Immunology 51, 517, 1984.

17. Mehta, K., and Lopez-Berestein, G. Expression of tissue transglutaminase in cultured monocytic leukemia (THP-1) cells during differentiation. Cancer Res. 46, 1388, 1986.

18. Mehta, K. Lopez-Berestein, G., Hersh, E. M., and Juliano, R. L. Uptake of liposomes and liposome-encapsulated muramyl dipeptide by human peripheral blood monocytes. J. Reticuloendothelial Soc. 32, 155. 1982.

19. Mehta, K., Lopez-Berestein, G., Moore, W. T., and Davies, P. J. A. Interferon-g requires serum retinoids to promote the expression of tissue transglutaminase in cultured human blood monocytes. J. Immunol. 134, 2053, 1985.

20. Mehta, K., Murtaugh, M. P., Juliano, R. L., and Davies, P. J. A. Phagocytosis inhibits the expression of tissue transglutaminase in mouse peritoneal macrophages J. Immunol. 132, 2552, 1984.

21. Moore, W. T., Murtaugh, M. P., and Davies, P. J. A. Retinoic acid induced expression of tissue transglutaminase in mouse peritoneal macrophages. J. Biol. Chem. 259, 12794, 1984.

22. Murtaugh, M. P., Arend, W. P., and Davies, P. J. A. Induction of tissue transglutaminase in human peripheral blood monocytes. J. Exp. Med. 159, 114, 1984.

23. Murtaugh, M. P., Dennison, O., Stein, J. P., and Davies, P. J. A. Retinoic acid induced gene expression in normal acid leukemic myeloid cells. J. Exp. Med. 163, 1325, 1986.

24. Murtaugh, M. P., Mehta, K., Johnson, J., Meyers, M., Juliano, R. I., and Davies, P. J. A. Induction of tissue transglutaminase in mouse peritoneal macrophages. J. Biol. Chem. 258, 11074, 1983.

25. Nelson, D. S. Macrophages as effectors of cell-mediated immunity. CRC Crit. Rev. Microbiol 1, 45, 1972.

26. Normann, S. J., and Weiner, R. Cytotoxicity of human peripheral blood monocytes. Cell. Immunol. 81, 413, 1983.

27. Norris, D. A., Morris R. M., Sanderson, R. J., and Kohler, P. F. Isolation of functional subsets of human peripheral blood monocytes. J. Immunol. 123, 166, 1979.

28. Olsson, I. L., and Brietman, T. R. Induction of differentiation of the human histiocytic lymphoma cell line U-937 by retinoic acid and cyclic adenosine 3', 5'-monophosphate inducing agents. Cancer Res. 42, 3924, 1982.

29. Peterson, P. A. Characteristics of a vitamin A transporting protein complex occurring in human serum. J. Biol. Chem. 246, 34, 1971.

30. Picker, L. J., Raff, H. V., Goldyne, M. E., and Stobo, J. B. Metabolic Heterogeneity among human monocytes and its modulation of $PGE_2$. J. Immunol. 124, 2557, 1980.

31. Rask, L., and Peterson, P. A. In vitro uptake of vitamin A from the retinol-binding plasma protein to mucosal epithelial cells from the monkey's small intestine. J. Biol. Chem. 251, 6360, 1976.

32. Roberts, A. B., and Sporn, M. B. Cellular biology and biochemistry of the retinoids, In The Retinoids, Vol. 2 (Sporn, M. B., Roberts A. B., and Goodman, D. S., Eds.) New York: Academic Press, p. 209, 1984.

33. Rothblat, G. H., Arborgast, L. Y., Quellett, L., and Howard, B. V. Preparation of delipidized serum proteins for use in cell culture systems. In Vitro 12, 554, 1976.

34. Schroff, G., Neumann, C., and Sorg, C. Transglutaminase as a marker for subsets of murine macrophages. Eur. J. Immuno. 11, 637, 1981.

35. Scott, K. F., Meyskens, F. L., Jr., and Russel, D. H. Retinoids increase transglutaminase activity and inhibit ornithine decarboxylase activity in Chinese ovary hamster cells and in melanoma cells stimulate to differentiate. Proc. Natl. Acad. Sci. USA, 79, 4053, 1982.

36. Turpin, J., Hester, J. P., Hersh, E. M., and Lopez-Berestein. G. Centrifugal elutriation as a method for isolation of large number of functionally intact human peripheral blood monocytes. J. Clin. Apheresis. 3, 111, 1986.

37. Turpin, J., Hersh, E. M., and Lopez-Berestein, G. Characterization of small and large human peripheral blood monocytes; effects of in vitro maturation on hydrogen peroxide release and on the response to macrophage activators. J. Immunol. 136, 4194, 1986.

38. Yuspa, S. Ben, T., and Litchi, U. Regulation of epidermal transglutaminase activity and terminal differentiation by retinoids and phorbol esters. Cancer Res. 43, 5707, 1983.

39. Yuspa, S., Ben, T., and Steinert, P. Retinoic acid induces transglutaminase activity but inhibits cornification of cultured epidermal cells. J. Biol. Chem. 257, 9906, 1982.

EXAMPLE 8

In vivo Administration

A. Materials and Methods

1. Liposomes and liposomal all-trans retinoic acid

Liposomal all-trans retinoic acid was prepared from lyophilized powder in bottles containing 3 mg of all-trans retinoic acid and 45 mg of a mixture of two phospholipids, dimyristoyl lecithin and dimyristoyl phosphatidylglycerol in a 3:7 ratio (Avanti Polar Lipids, Birmingham, Ala.). Immediately before use, liposomal all-trans retinoic acid was reconstituted by adding 3 ml of normal saline to each bottle and agitating the suspension on a vortex mixer for 2–3 min. The reconstituted preparation consisted of multilamellar liposomes (average size, 3.1 $\mu$m).

2. Animals

Six-week-old Lewis rats (Charles River. Wilmington, Mass.) were used for these studies. Groups of eight female rats each were administered 5 mg/kg body weight of either all-trans retinoic acid (mixed with mineral oil) orally or liposomal all-trans retinoic acid, intravenously (in tail vein). Each rat received a total of 15 doses, twice a week, 3–4 days apart, for 7 weeks. Blood samples of 150 $\mu$l were collected from the tail vein 5, 30, 60, and 90 minutes following administration of the last dose and analyzed for all-trans retinoic acid levels by HPLC. Blood samples were also collected 60 min after administration of the first and sixth dose and analyzed for all-trans retinoic acid. Ninety minutes after the last dose, all the animals were killed and blood samples of 3 ml were collected to study the hematologic and blood chemistry parameters. Sections of tissues were collected on dry ice for further processing or were fixed in formalin for histopathologic analysis.

3. Cellular retinoic acid-binding protein (CRABP)

Liver samples were collected 90 minutes after the last dose and processed individually. Total CRABP (CRABP I and II) levels were quantitated by slab gel electrophoresis. Briefly, cytoplasmic proteins were extracted and 100–200 $\mu$g protein were incubated overnight at 4° C. in a 100 $\mu$l solution of 50 nM $^3$[H]-all-trans retinoic acid (specific activity 49.3 Ci/mmol; and 2 mM dithiothreitol with or without 200-fold excess of unlabeled all-trans retinoic acid. Reactants were fractionated over vertical slab gel polyacrylamide electrophoresis under native conditions. After electrophoresis the gel was divided into lanes and cut into 5 mm bands; radioactivity was assessed in a liquid scintillation counter. Specific binding was determined from the radioactivity recovered with or without the 200-fold excess of unlabeled retinoid.

4. In vitro metabolism of all-trans retinoic acid

Liver samples obtained from the animals at the time of death were rinsed in ice-cold saline and homogenized individually in a 3-fold volume of 0.25 M sucrose 0.05 M Tris-HCl (pH 7.4) using a Teflon® glass homogenizer. Microsomes were isolated by differential centrifugation at (10,000 g for 20 min; 100,000 g, 60 min). The microsomal pellet was suspended in 0.05 M Tris-HCl (pH 7.4), portioned into aliquots and stored at −70° C. Protein content was determined by Biorad Protein Assay using bovine serum albumin as the standard.

The assay buffer and conditions used for determining the ability of microsomes to metabolize [carboxyl-$^{14}$C] all-trans retinoic acid (specific activity 13.7 Ci/nmol) were essentially the same as those described by Van Wauwe et al., *J. Pharmac. exp. Ther.*, Vol. 245, 718. After 30 min, the reaction was stopped by cooling and the samples were lyophilized to dryness. Dried residues were extracted with methanol containing butylated hydroxyanisole (0.05%, v/v), and the extracts were evaporated and redissolved in small volumes of methanol (25–50 $\mu$l). All-trans retinoic acid and metabolites were then separated by thin layer chromatography by spotting 20,000–25,000 cpm on 0.25-mm silica-coated plastic sheets, and developing in a solution of benzene, chloroform, and water (4:1:1). The radioactive spots were located by spraying, the plates with EN$^3$Hance (New England Nuclear) and autoradiography. The radioactive bands were scraped out, extracted with Solvable (New England Nuclear) and counted in a scintillation counter. The extent of all-trans retinoic acid metabolism was determined from the proportions of cpm in appropriate zones and expressed as a percentage of the total amount of radioactivity recovered.

5. HPLC analysis

The extent of all-trans retinoic acid metabolism by isolated liver microsomes was also determined by HPLC analysis. The reactants were lyophilized and the residues were extracted twice with 2 ml of methanol containing 0.05% butylated hydroxyanisole (Sigma Chemical Co., St. Louis, Mo.). After centrifugation, the supernatants were aspirated and evaporated. The resulting pellets were re-extracted in a methanol:dichloromethane solution (75:25) and again evaporated in vacuo. More than 80% of the added all-trans retinoic acid was recovered. The final pellet was mixed with 200 $\mu$l of mobile phase for reverse-phase HPLC. A portion of each sample (150 $\mu$l) was analyzed on a 10-$\mu$m $C_{18}$ Bondapack column (3–9×300 mm; Waters Associates, Farmingham, Mass.). Samples were eluted with a solution of methanol, water, and formic acid (60:40:0.05) containing 10 mM ammonium acetate at a flow rate of 2 ml/min. After 20 min, the solvent was changed to 100% methanol in order to elute all-trans retinoic acid.

Reverse phase HPLC was also used for determining the blood concentrations of all-trans retinoic acid. All procedures were performed in a room with the lights dimmed. Whole blood samples (200 $\mu$l) were extracted twice (1 ml each) with methanol. After centrifugation, the supernatants were vacuum-dried and the dried pellets were reconstituted in 200 $\mu$l of methanol. The recovery of all-trans retinoic acid under these conditions was calculated to be 85%±7%. The HPLC system included two pumps and a Zorbax-C8 reverse phase column (4 mm×8 cm; Supelco, Pa.). The mobile phase consisted of a linear gradient between solvent A (THF and water (25:75) containing 0.04% ammonium acetate pH 4) and solvent B (100% THF) during a 16 minute run at a flow rate of 1.8 ml/min. The absorbance was monitored at 346 nm. Retention time for all-trans retinoic acid under these conditions was approximately 9.8 minutes.

6. Determination of P450 levels

Cytochrome P450 levels in liver microsomes were determined spectrophotometrically. The assay system is based on the carbon monoxide (CO) difference spectra of dithionite-reduced samples, assuming a value of 91 mM/cm for the molar extinction increment between 450 and 490 m$\mu$. The P450 activity was calculated by the following formula: (change in absorbance between dithionite-reduced sample and CO sample alone)/91×1000: it was expressed as nm/mg protein.

7. Statistical analysis

The mean values for the groups were analyzed by using Student's t-test for paired samples.

B. Results

Hematologic and blood chemistry analysis of samples drawn 90 min. after administration of the last dose of liposomal or non-liposomal all-trans retinoic acid, summarized in Table 6, revealed no significant changes, except that the number of circulating segmented neutrophils was significantly decreased in animals treated with either drug formulation. This decrease in circulating neutrophils was more pronounced in rats treated with non-liposomal all-trans retinoic acid than in those treated with liposomal all-trans retinoic acid or in untreated controls ($p<0.05$). Similarly, no appreciable change was observed in most of the blood chemistry parameters studied, except both the non-liposomal all-trans retinoic acid and liposomal all-trans retinoic acid-treated rats showed slight increases in alkaline phosphatase levels (Table 6).

TABLE 6

HEMATOLOGICAL AND BLOOD CHEMISTRY PARAMETERS
OF RATS FOLLOWING LONG-TERM ADMINISTRATION
OF FREE ATRA AND L-ATRA*

|  | Control | ATRA (p.o.) | L-ATRA (i.v.) |
|---|---|---|---|
|  |  | (5 mg/kg body weight) | |
| Hematological parameters | | | |
| WBCs (× $10^3$/mm$^3$) | 5.1 ± 1.9 | 4.3 ± 1.3 | 6.3 ± 1.8 |
| RBCs (× $10^6$/mm$^3$) | 7.1 ± 0.1 | 7.0 ± 0.3 | 6.6 ± 0.5 |
| Hgb (gm/dl) | 13.5 ± 0.4 | 13.3 ± 0.6 | 12.6 ± 1.0 |
| Plts (× $10^3$/mm$^3$) | 607.0 ± 106 | 577.0 ± 252 | 644.0 ± 107 |
| Segs (× $10^3$/mm$^3$) | 59.3 ± 4.9 | 28.6 ± 8.6 | 46.0 ± 14.3 |
| Lymph (× $10^3$/mm$^3$) | 40.0 ± 4.3 | 69.0 ± 10.0 | 54.1 ± 9.0 |
| Blood chemistry parameters | | | |
| Electrolytes (mEq/L) | | | |
| $K^+$ | 3.8 ± 0.2 | 4.1 ± 0.2 | 3.8 ± 0.4 |
| $Na^+$ | 142.6 ± 0.6 | 142.7 ± 0.9 | 142.5 ± 1.3 |
| $Cl^-$ | 99.3 ± 1.5 | 99.0 ± 2.5 | 98.7 ± 3.5 |
| Creatinine (mg %) | 0.43 ± 0.05 | 0.56 ± 0.1 | 0.51 ± 0.1 |
| BUN (mg/dl) | 21.7 ± 3.2 | 22.7 ± 3.1 | 22.4 ± 4.7 |
| SGOT (IU) | 171.0 ± 33.1 | 144.4 ± 55.2 | 131.9 ± 72.1 |
| SGPT (IU) | 62.3 ± 7.6 | 76.5 ± 34.0 | 73.9 ± 17.9 |
| Alk. Phos. (IU) | 144.7 ± 5.0 | 188.6 ± 23.3 | 203.0 ± 20.7 |
| Bilirubin (mg %) | 0.2 ± 00 | 0.16 ± 0.05 | 0.13 ± 0.05 |

*Groups of rats were administered p.o. free ATRA or i.v. L-ATRA twice a week for 7 weeks (15 doses). After the last dose, blood was collected and analyzed for various parameters. The results shown are the average values from four to eight rats ± standard deviation from the mean.
WBCs, white blood cells; RBCs, red blood cells; Hgb, hemoglobin; Plts, platelets; Segs, segmented neutrophils; Lymph, lymphocytes; BUN, blood urea nitrogen; SGOT, serum glutamic oxaloacetic transaminase; SGPT, serum glutamic pyruvic transaminase; Alk. Phos., alkaline phosphatase.

Microscopic examination of tissue sections from the liver, lung, spleen, brain, ovary, skin, kidney, and bone marrow of the treated rats revealed no significant changes in the histopathologic characteristics. Interestingly, spleens from seven of the eight liposomal all-trans retinoic acid-treated subjects showed the presence of numerous small vacuoles throughout the red pulp area. These structures might represent entrapped liposomes that were removed during processing. They were seen throughout the sinusoids and in phagocytes. No such vacuolization was observed in animals that were treated with non-liposomal all-trans retinoic acid or in control animals treated with saline alone.

FIG. 12(A) shows the levels of all-trans retinoic acid in the blood 60 min after oral administration of non-liposomal all-trans retinoic acid or i.v. administration of liposomal all-trans retinoic acid. In general, these blood levels were higher in rats treated with liposomal all-trans retinoic acid than in those treated with non-liposomal all-trans retinoic acid. This difference became most striking after 7 weeks of continuous drug treatment. The mean level of all-trans retinoic acid in the blood of rats treated with non-liposomal all-trans retinoic acid decreased from 3.01±0.33 μg/ml on day 1 to 1.97±0.17 μg/ml (p<0.01) after 7 weeks of treatment, whereas the mean blood all-trans retinoic acid levels of rats treated with liposomal all-trans retinoic acid did not change significantly. The mean all-trans retinoic acid concentration on day 1 (4.42±1.2 μg/ml) was similar to that at the end of treatment (4.41±0.2 μg/ml). Also studied was blood clearance of all-trans retinoic acid following administration of the last dose of all-trans retinoic acid. Results shown in FIG. 12(B) demonstrate that all-trans retinoic acid could be detected in the blood by HPLC 30 minutes after ingestion of non-liposomal all-trans retinoic acid. The drug reached its maximum level (2.01±0.24 μg/ml) after 60 min and remained constant for at least 90 min (1.97±0.17 μg/ml). In contrast, significantly higher concentrations of all-trans retinoic acid (7.57±1.2±μg/ml) were observed in the blood 5 min following i.v. administration of liposomal all-trans retinoic acid. The clearance of liposomal all-trans retinoic acid from blood occurred in two phases, the initial rapid phase ($t_{1/2}\alpha$=16 min) followed by a slower terminal phase ($t_{1/2}\beta$=55 min). Nonetheless, blood levels of the drug were significantly higher in subjects treated with liposomal all-trans retinoic acid at each time point studied (p<0.001) than in animals administered non-liposomal all-trans retinoic acid.

Particularly addressing FIG. 12: Blood concentrations of all-trans retinoic acid in rats after 7 weeks treatment with non-liposomal all-trans retinoic acid or liposomal all-trans retinoic acid are presented. FIG. 12(A) presents data from groups of eight rats administered (5 mg/kg body weight) either p.o. non-liposomal all-trans retinoic acid (cross-hatched bars) or i.v. liposomal all-trans retinoic acid (solid bars) twice a week for a total of 7 weeks. Blood samples (200 μl) were collected 60 min after the administration of the first, sixth, and fifteenth doses, and 150 μl aliquots of the blood were analyzed for all-trans retinoic acid by HPLC. In FIG. 12(B) data is presented following administration of the last dose. Blood samples were collected from animals treated with non-liposomal all-trans retinoic acid (open circles) or liposomal all-trans retinoic acid (solid dots) at indicated time intervals and analyzed by HPLC for all-trans retinoic acid content. The results shown are mean plasma drug concentrations in six rats±S.D.

Because cytochrome P450-dependent accelerated catabolism and induction of CRABP have been implicated in the acquisition of clinical resistance to all-trans retinoic acid, a determination was made that the CRABP and cytochrome P450 levels in liver tissues of rats that had been treated with either all-trans retinoic acid formulation was mad. No appreciable differences in CRABP levels were observed between liver samples of rats that had been treated with non-liposomal all-trans retinoic acid or liposomal all-trans retinoic acid and untreated controls. Similarly, there were no significant changes in total cytochrome P450 levels in liver microsomes from rats treated with non-liposomal all-trans retinoic acid (0.63±0.13 nmol/mg; n=7) or liposomal all-trans retinoic acid (0.59±0.01 nmol/mg; n=7) or untreated rats (0.68±0.15 nmol/mg; n=6).

Figure 13B:
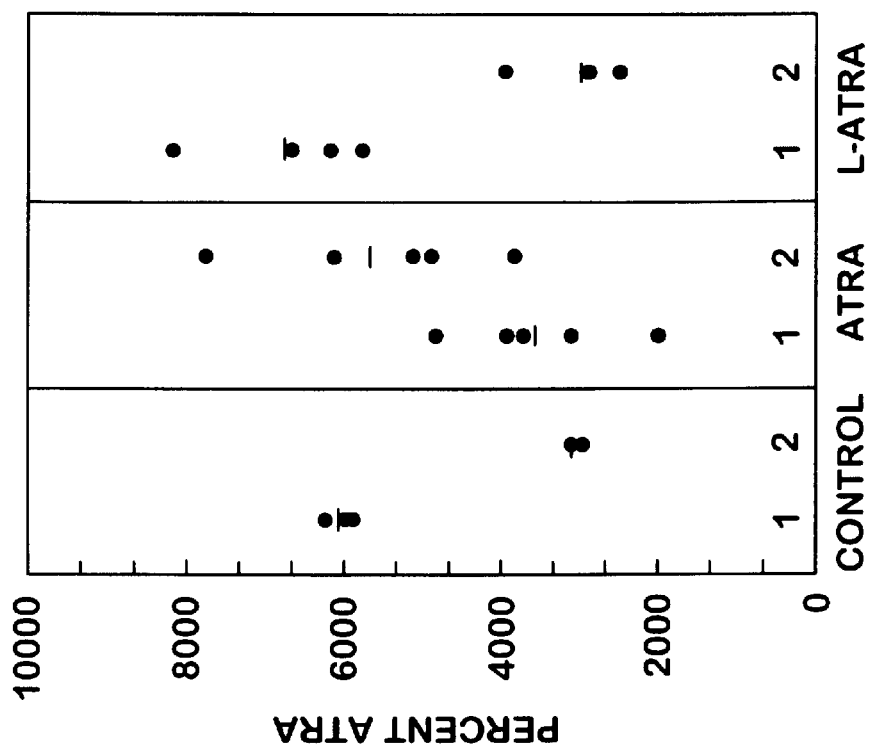
FIG. 13(B) shows radioactivity (cpm) of all-trans retinoic acid or its polar metabolites (as discussed in association with FIG. 12(A)) as gathered from five animals.

In vitro, however, the liver microsomes isolated from rats that were treated with non-liposomal all-trans retinoic acid exhibited significant rapid catabolism of all-trans retinoic acid. Incubation of [$^{14}$C]all-trans retinoic acid with isolated liver microsomes in the presence of NADPH resulted in rapid conversion of all-trans retinoic acid into two polar products as determined by thin layer chromatography. Incubation under similar conditions of liver microsomes from untreated rats or rats treated with liposomal all-trans retinoic acid revealed a significantly slower rate of metabolism of all-trans retinoic acid into these polar metabolites. When combined, these metabolites accounted for about 33±0.8% of the microsomes from untreated rats and 28.8±2.57% of those from liposomal all-trans retinoic acid-treated rats, whereas they accounted for 57±11.2% of the microsomes from animals treated with non-liposomal all-trans retinoic acid. (FIG. 13(A)) Individual values for intact all-trans retinoic acid and its polar metabolites generated in the presence of NADPH by liver microsomes that were isolated from five different rats treated with either non-liposomal all-trans retinoic acid or liposomal all-trans retinoic acid or from three untreated rats are shown in FIG. 13(B). Microsomes from all liposomal all-trans retinoic acid-treated and control animals induced much slower catabolism of all-trans retinoic acid than those from rats administered non-liposomal all-trans retinoic acid (FIG. 13(B)). Liver microsomes isolated from rats that were treated with "empty liposomes" without all-trans retinoic acid showed rates of conversion of all-trans retinoic acid to its metabolites similar to those of the untreated controls. The reaction products generated by incubating all-trans retinoic acid in the presence of NADPH and liver microsomes were further analyzed by reverse phase HPLC. Results of that HPLC analysis demonstrated that microsomes from rats treated with non-liposomal all-trans retinoic acid converted the drug into four major products (retention times, 7.5–11.5 min). Two of the metabolites were eluted at the same positions as authentic 4-keto all-trans retinoic acid (retention time, 7.8 min) and 4-hydroxy all-trans retinoic acid (retention time, 9.5 min). Incubation of microsomes from rats injected with liposomal all-trans retinoic acid also converted all-trans retinoic acid into polar metabolites, but these metabolites were different, quantitatively and to some extent qualitatively, from those in the group treated with non-liposomal all-trans retinoic acid. For example, the metabolite that eluted at 11.1 min from the non-liposomal all-trans retinoic acid microsome reaction mixture was not seen in the liposomal all-trans retinoic acid microsome reaction mixture. Similarly, the amounts of three other products (retention times, 7.8–9.6 min), were much smaller in the reaction mixture incubated with microsomes from liposomal all-trans retinoic acid-treated rats.

Figure 13A:
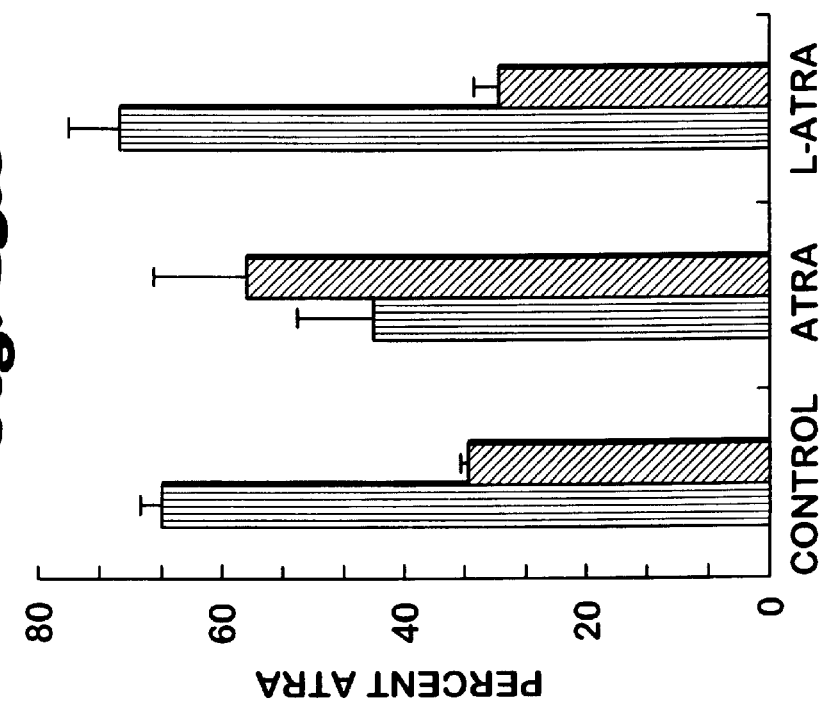
FIG. 13(A) shows the percentage of all-trans retinoic acid metabolized by isolated liver microsomes to animals exposed to 7 weeks of treatment with all-trans retinoic acid, either liposomal i.v. or oral.

Addressing FIG. 13: The effect of long-term all-trans retinoic acid administration on drug metabolism by liver microsomes is presented. FIG. 13(A), at the end of the 7 week treatment period, animals were killed and their liver microsomes isolated. The ability of microsomes to metabolize in vitro [$^{14}C$]all-trans retinoic acid was then determined by incubating microsomes in the presence of NADPH and radiolabeled all-trans retinoic acid (50 nM). The reaction products were fractionated by thin layer chromatography and extent of drug metabolism was determined by counting the metabolite fractions. Results are expressed as a percentage of all-trans retinoic acid metabolized to polar products (cross-hatched bars) or percentage of all-trans retinoic acid remaining intact (solid bars). The vales shown are averages from five rats±S.D. FIG. 13(B) presents radioactivity (cpm) recovered from intact all-trans retinoic acid (lane 1) or its polar metabolites (lane 2), as discussed in FIG. 13(A), were plotted individually for five different rats.

Non-liposomal all-trans retinoic acid has been ineffective in permanently maintaining the remission state of acute promyelocytic leukemia ("APL"). Even when all-trans retinoic acid administration is continued after remission has been achieved, many APL patients still experience relapse. Clearly, some mechanism of resistance develops in relapsed patients whereby the ability of all-trans retinoic acid to induce cellular differentiation is diminished substantially. Several in vitro studies have attempted to explain the evolution of this resistance mechanism, which can be induced in culture after continuous exposure to elevated concentrations of retinoid or carotenoid. Interesting recent clinical pharmacological evidence regarding all-trans retinoic acid resistance (Muindi et al., Blood, 79:299 (1992); Cancer Res., 52:2138 (1992)) concluded that the reason for the eventual occurrence of this retinoid resistance during all-trans retinoic acid therapy is progressively decreasing plasma drug concentration levels. In most subjects the onset of the decrease in plasma drug concentration levels is within 2–6 weeks after beginning treatment. Although these lower all-trans retinoic acid plasma levels cannot sustain the differentiation effects on leukemic cells in vivo, in culture the leukemic cells from these patients continue to demonstrate cytodifferentiation sensitivity to all-trans retinoic acid. This resistance is not seen with other retinoids such as isotretinoin or etretinate.

An advantage of the liposomal all-trans retinoic acid of this invention is that the lipid formulation bypasses the clearance mechanism that evolves in the livers of patients treated with the oral formulation. Liposomal formulation is thus not be subject to the same relapse rates as have been demonstrated in clinical trials of the non-liposomal formulation. In addition, the toxic effects of liposomal all-trans retinoic acid should be less severe than those associated with non-liposomal all-trans retinoic acid because liposome encapsulation of all-trans retinoic acid decreases direct exposure of the drug during circulation to levels below the orally administered toxic dose. The latter allows greater total exposure of the drug on initial dose accompanied by slower clearance of the all-trans retinoic acid from the site of stem cell seeding.

All-trans retinoic acid is metabolized by a hydroxylation reaction of the cyclohexenyl ring, to produce 4-hydroxy metabolites which are further oxidized to the 4-oxo metabolites. The hydroxylation of all-trans retinoic acid to the 4-oxo-all-trans retinoic acid metabolite is mediated by cytochrome P450-dependent enzymes. The most favored explanation of the pharmacological mechanism of all-trans retinoic acid resistance is that continuous all-trans retinoic acid treatment acts to induce catabolic enzymes that are responsible for conversion of the drug. Animal studies in which all-trans retinoic acid was administered in combination with cytochrome P450 enzyme inhibitors (e.g, ketoconazole or liarozole) showed a significant prolonging of the all-trans retinoic acid plasma half life, thereby supporting the contention of accelerated enzymatic degradation. The results reported here confirm the previous observations that chronic oral administration of all-trans retinoic acid in rats results in decreased drug plasma concentrations, whereas i.v. administration of liposomal all-trans retinoic acid at a similar dose and regimen did not alter the pharmacological behavior of the drug and the blood levels remained stable throughout the study period (FIG. 12). The observed differences in pharmacological behavior of the two formulations were consistent with induction of an enzymatic process. Although no differences were observed in total P450 levels in rats treated with either formulation, microsomes from rats treated with non-liposomal all-trans retinoic acid metabolized the drug much more rapidly than those from rats treated with liposomal all-trans retinoic acid (FIG. 13).

Another factor that might contribute to the retinoid relapse phenomenon involves the role of high affinity retinoic acid-binding, proteins CRABP I and II. These proteins are believed to mediate the transfer of the retinoid from cytoplasm to the nucleus of the cell. Increased levels of CRABP may cause the pooling of retinoids in tissues resulting in low plasma levels and accelerated clearance of the drug from the circulation. In normal body tissues the expression of CRABP is thought to increase with continuous exposure to retinoids. An increase in CRABP has been documented in human skin as a result of repeated topical application of all-trans retinoic acid. A similar increase in skin CPABP levels was also observed by Adamson et al. in rhesus monkeys following chronic i.v. administration of all-trans retinoic acid.

These authors concluded that the increase in CRABP expression was not related to the increase in plasma drug clearance observed with continuous all-trans retinoic acid administration, but rather was related to catabolic enzyme induction. In the present data, no increase in levels of liver CRABP was observed in rats administered either non-liposomal all-trans retinoic acid or liposomal all-trans retinoic acid on a continuous basis.

The results of Example 8 study, coupled with the following data obtained in clinical trials discloses that long term oral administration of all-trans retinoic acid is associated with the rapid clearance of the drug from plasma that, in turn, contributes to the relapse of the disease in APL patients, strongly supports the rationale of using liposomal all-trans retinoic acid to induce long-term remissions in APL patients.

EXAMPLE 9

In vivo i.v. Liposomal All-trans Retinoic Acid Subjects with Hematological Malignancies Liposomal all-trans retinoic acid was administered i.v. over one-half hour every other day for 28 days to human subjects with hematological malignancies, including T cell cutaneous lymphoma and APL. Doses investigated were 15 mg/m$^2$ (5 points), 30 mg/m$^2$ (3 points), 60 mg/m$^2$ (3 points), 75 mg/m$^2$ (7 points), and 90 mg/m$^2$ (3 points). No dose limiting toxicity has been observed.

Two efficacious responses have been observed. One modestly favorable response was in a subject with T cell cutaneous lymphoma in a patient considered resistant to oral all-trans retinoic acid. This patient is presently receiving a second 28 day treatment cycle.

A subject with APL in first relapse 10 months after receiving oral all-trans retinoic acid in three weeks of the liposomal treatment of the present invention displayed a rising white count and evidence of increased cellular differentiation in both the blood and the marrow.

Pharmacokinetic drug level data was also compared to published data for all-trans retinoic acid. As taken form Trump et al., *ASCO proc.*, Vol. 13, page 241 (1994) referencing a with prostate cancer, all-trans retinoic acid (non-liposomal) administered orally at 50 mg/m$^2$, twice per day for 14 days yielded a $C_{max}$ in ng/ml on day 1 of 307 and day 14 of 144. The AUC in $\mu$g hr/ml was 0.693 on day 1 and 0.250 on day 14. A substantially distinct result was obtained using the liposomal all-trans retinoic acid of the present invention in one patient administered 60 mg/m$^2$ every other day for 15 doses i.v. The $C_{b0}$ (the concentration in blood at the conclusion of i.v. administration, time 0) in $\mu$g/ml was 6.8 on day one and 7.0 on day 15 after the eighth dose. The AUC in $\mu$g/ml×min was 466 on day 1 and 580 on day 15. Converting to $\mu$g hr/ml these values are 7.76 and 9.66 respectively.

The clearance of liposomal all-trans retinoic acid was found to closely fit ($r^2$>0.9) a two compartment mathematical model in 14 of 22 complete analyses, and was best fit by a one compartment model in 8 of 22 studies. Where present, alpha-phase half-lives ranged from 56±20 minutes at the 15 mg/m$^2$ dose level to 116±43 minutes at the highest level analyzed, 75 mg/m$^2$. There were no statistically significant differences (Student's t-test at p<0.05) in the calculated half lives between day 1 and 15. In addition, there were no significant differences in half-lives at the different dose levels studied.

The apparent volume of distribution (Vd) was 25+2 liters at the 15 mg/m$^2$ dose level (day 1) suggesting rapid distribution into a space approximating total body water. As observed with the half-life data, there were no statistically significant differences in $V_d$ between subjects at the different dose levels or between patients treated on day 1 or 15. Both the $C_{b0}$ and the extrapolated area under the concentration curve ($C_{xt}$) were found to increase proportionately over the dose range studied. Further, this range was not statistically different from Day 1 to 15. These pharmacokinetic studies disclose that the liposomal formulation of the present invention maintains blood level and does not exhibit the reduction in blood levels(retinoid resistance), or other parameters associated with prolonged oral administration of all-trans retinoic acid. Further, in the instant study, the absence of dose-dependent and time-dependent increases in pharmacokinetic parameters indicate no apparent saturation of drug clearance mechanisms.

\* \* \*

The preceding description is intended to illustrate specific embodiments of the present invention. It is not intended to be an exhaustive list of all possible embodiments. Person skilled in the relevant field will recognize that modifications could be made to the specific embodiments which have been disclosed, that would remain within the scope of the invention.

We claim:

1. A pharmaceutical unit dosage formulation of a retinoid, which comprises a retinoid, liposomes, and intercalated triglyceride; where the retinoid is present in cancer inhibitory amount and substantially uniformly distributed with the lipid in the liposomes, where the molar ratio of retinoid to lipid is at least about 15:85, where the triglyceride is at least about 15% by weight of the composition, and where the composition is stable in an aqueous environment and retinoic acid resistance-avoiding.

2. The formulation of claim 1, where the retinoid is retinoic acid.

3. A retinoic acid resistance-avoiding method of inhibiting the growth of cancer cells comprising administering to a living subject a therapeutically effective amount of a retinoid composition which comprises a retinoid, lipid, and intercalated triglyceride; where the retinoid is substantially uniformly distributed within the lipid and the triglyceride in the form of liposomes, where the molar ratio of retinoid to lipid is at least about 15:85, where the triglyceride is at least about 15% by weight of the composition, and where the composition is stable in an aqueous environment.

4. The method of claim 3, where the retinoid is retinoic acid.

5. The method of claim 3 comprising administering said retinoid composition in doses administered over a period of at least one-half hour.

6. The method of claim 3 comprising administering said retinoid composition at a frequency of about every other day or less frequent.

\* \* \* \* \*

UNITED STATES PATENT AND TRADEMARK OFFICE
CERTIFICATE OF CORRECTION

PATENT NO. : 6,200,597 B1
DATED : March 13, 2001
INVENTOR(S) : Kapil Mehta et al.

Page 1 of 1

It is certified that error appears in the above-identified patent and that said Letters Patent is hereby corrected as shown below:

<u>Title page,</u>
Item [73], Assignees, please delete "Aronex Pharmaceuticals, Inc., both of Austin TX" and insert -- Austin, TX, Aronex Pharmaceuticals, Inc., The Woodlands, TX -- therefor.

Signed and Sealed this

Fourteenth Day of May, 2002

*Attest:*

JAMES E. ROGAN
*Attesting Officer*    *Director of the United States Patent and Trademark Office*